(12) United States Patent
Solar et al.

(10) Patent No.: US 8,721,592 B2
(45) Date of Patent: May 13, 2014

(54) VARIABLE LENGTH CATHETER FOR DRUG DELIVERY

(75) Inventors: Ronald J. Solar, San Diego, CA (US); Yoav Shaked, Moshav Mishmeret (IL); Glen Lieber, Poway, CA (US)

(73) Assignee: ThermopeutiX, Inc., San Diego, CA (US)

( * ) Notice: Subject to any disclaimer, the term of this patent is extended or adjusted under 35 U.S.C. 154(b) by 265 days.

(21) Appl. No.: 13/151,378

(22) Filed: Jun. 2, 2011

(65) Prior Publication Data

US 2011/0282195 A1   Nov. 17, 2011

Related U.S. Application Data

(60) Continuation-in-part of application No. 13/080,667, filed on Apr. 6, 2011, now abandoned, which is a continuation-in-part of application No. 12/731,222, filed on Mar. 25, 2010, now Pat. No. 8,109,897, which is a division of application No. 11/338,892, filed on Jan. 25, 2006, now Pat. No. 7,704,220.

(51) Int. Cl.
*A61M 29/00* (2006.01)
*A61M 31/00* (2006.01)

(52) U.S. Cl.
USPC ............. 604/101.01; 604/102.01; 604/103.01

(58) Field of Classification Search
USPC ............. 604/101.01, 101.02, 101.04, 101.05, 604/102.01, 102.02, 103.01, 103.04
See application file for complete search history.

(56) References Cited

U.S. PATENT DOCUMENTS

| | | | |
|---|---|---|---|
| 4,655,746 A | 4/1987 | Daniels et al. | |
| 4,883,459 A | 11/1989 | Calderon | |
| 4,911,163 A | 3/1990 | Fina | |
| 5,059,178 A | 10/1991 | Ya | |
| 5,281,200 A | 1/1994 | Corso, Jr. et al. | |
| 5,320,605 A * | 6/1994 | Sahota | 604/101.01 |
| 5,462,529 A | 10/1995 | Simpson et al. | |
| 5,919,163 A | 7/1999 | Glickman | |
| 6,126,635 A | 10/2000 | Simpson et al. | |
| 6,706,013 B1 | 3/2004 | Bhat et al. | |
| 2002/0188253 A1 | 12/2002 | Gordon et al. | |
| 2004/0236350 A1 | 11/2004 | Lewis et al. | |
| 2005/0004503 A1 | 1/2005 | Samson et al. | |
| 2005/0059930 A1 | 3/2005 | Garrison et al. | |
| 2010/0082012 A1 * | 4/2010 | Hattangadi et al. | 604/509 |

FOREIGN PATENT DOCUMENTS

| | | |
|---|---|---|
| JP | 0002683750 | 1/1990 |
| JP | 1993220215 | 8/1993 |
| JP | 1997511155 | 11/1997 |
| JP | 2002501792 | 1/2002 |
| JP | 2004305251 | 11/2004 |
| WO | WO 00/74749 | 12/2000 |
| WO | WO 2004/075928 | 9/2004 |

* cited by examiner

*Primary Examiner* — Manuel Mendez
(74) *Attorney, Agent, or Firm* — Daniel J. Swirsky; AlphaPatent Associates Ltd.

(57) ABSTRACT

A system and method for localized delivery of a therapeutic or diagnostic agent within a vessel is provided. The system and method provide for adjustability of the length of the treatment area and for reducing of pressure within the treatment area. A catheter system includes an inner elongated element, an outer elongated element positioned coaxially with respect to the inner elongated element, and a blood-release element at a distal end of the inner elongated element. A proximal occlusion element is positioned at the distal end of the outer elongated element, proximal to an outlet port. A distal occlusion element is positioned at a distal end of the inner elongated element. The distal end of the inner elongated element is distal to and movable with respect to the outer elongated element distal end.

19 Claims, 31 Drawing Sheets

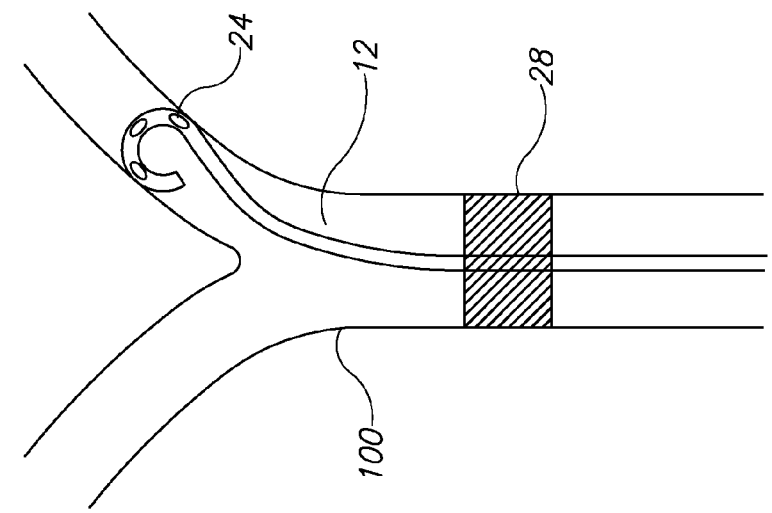
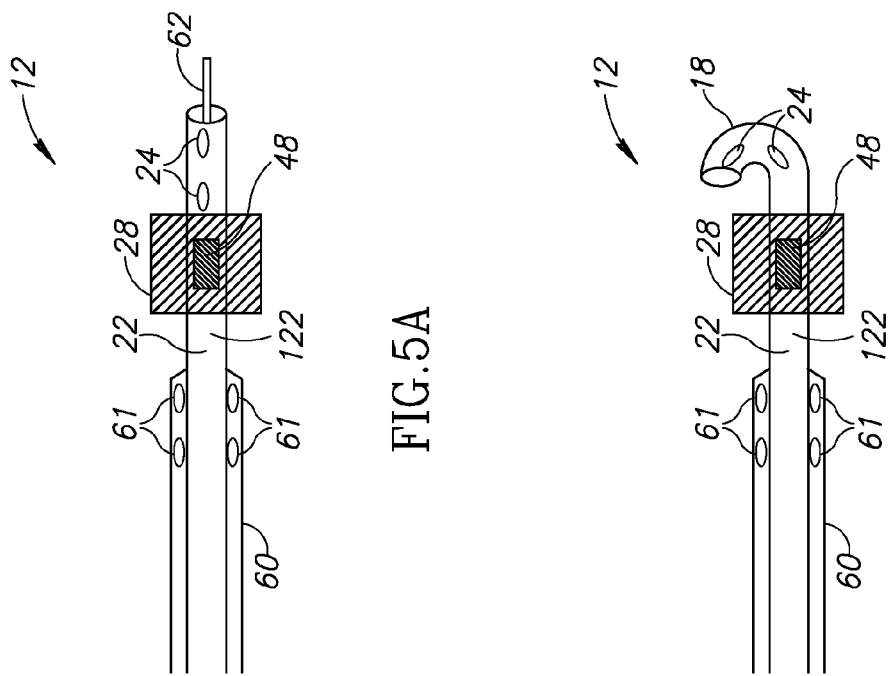
FIG.5A
FIG.5B
FIG.5C

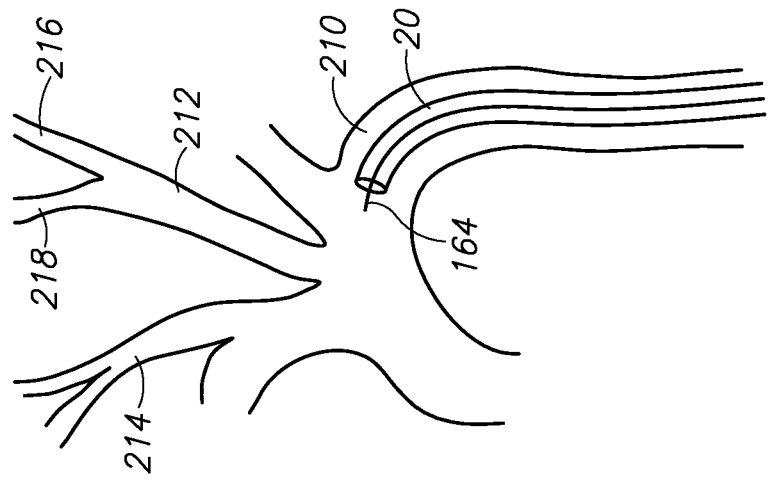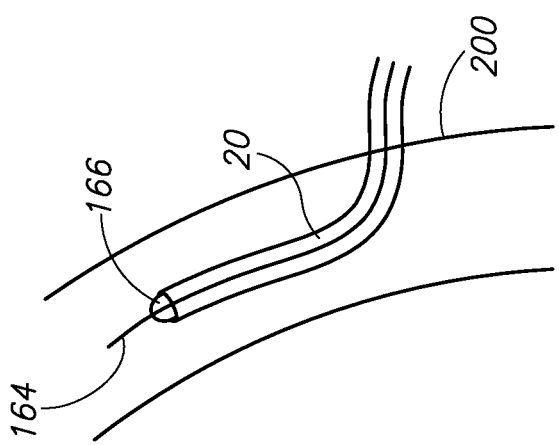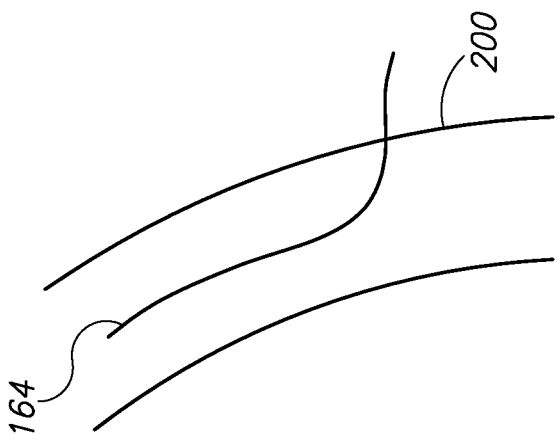

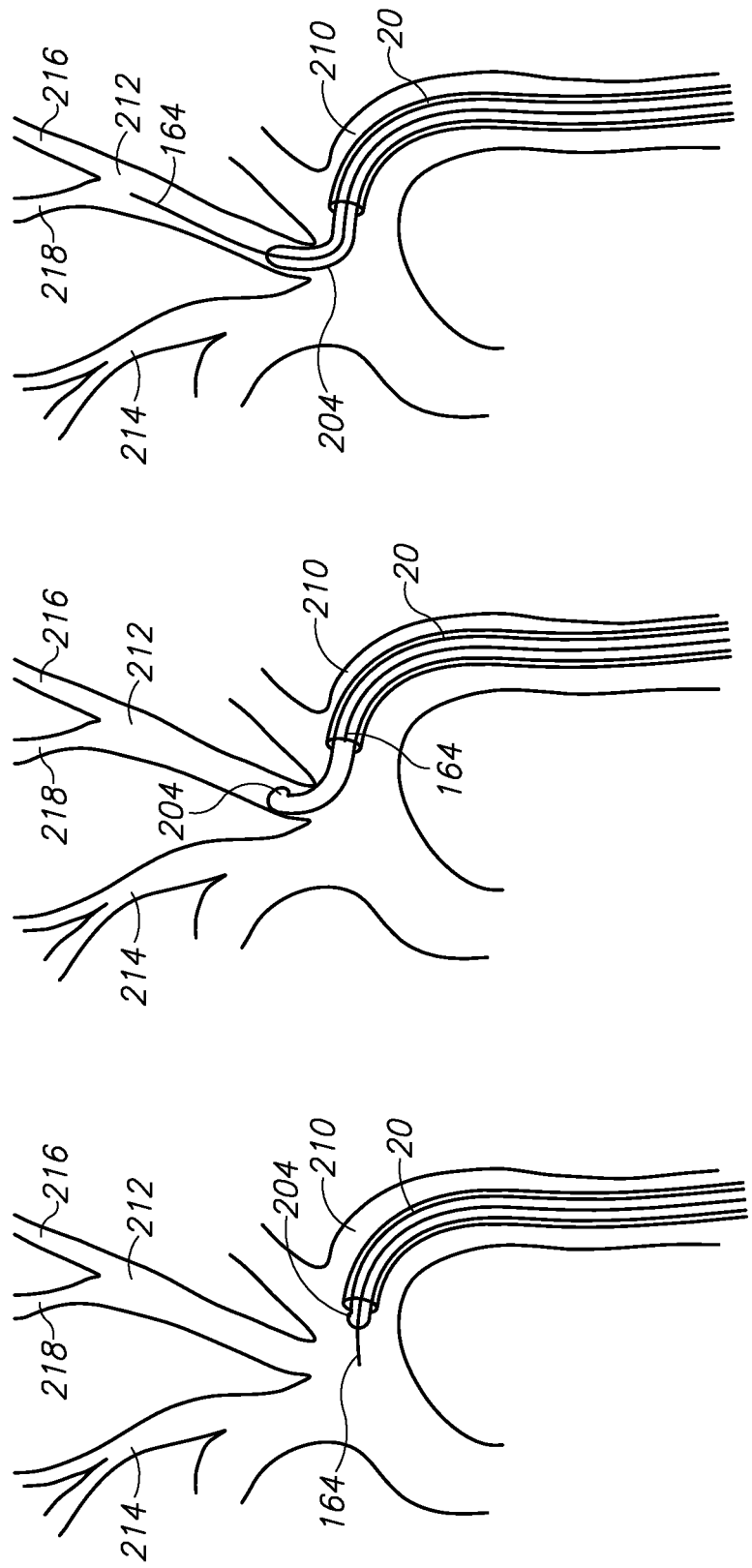

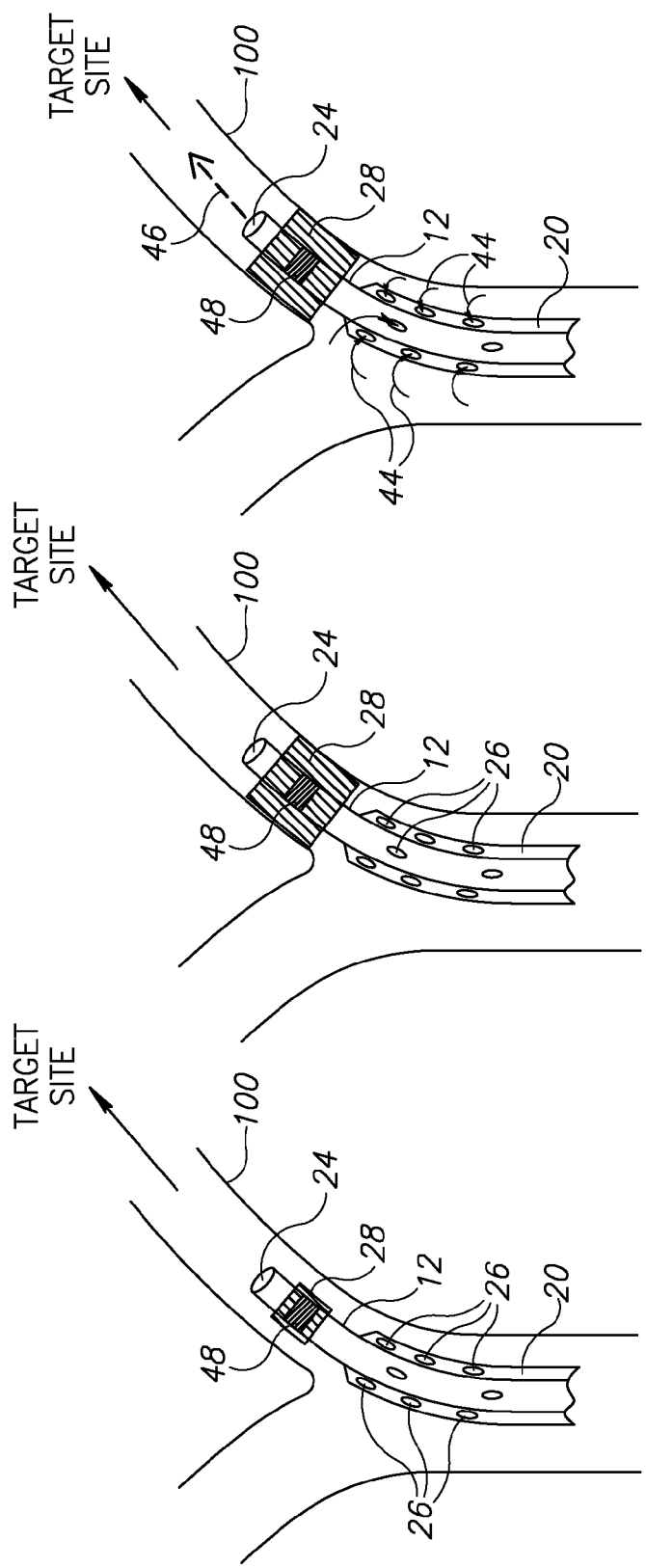

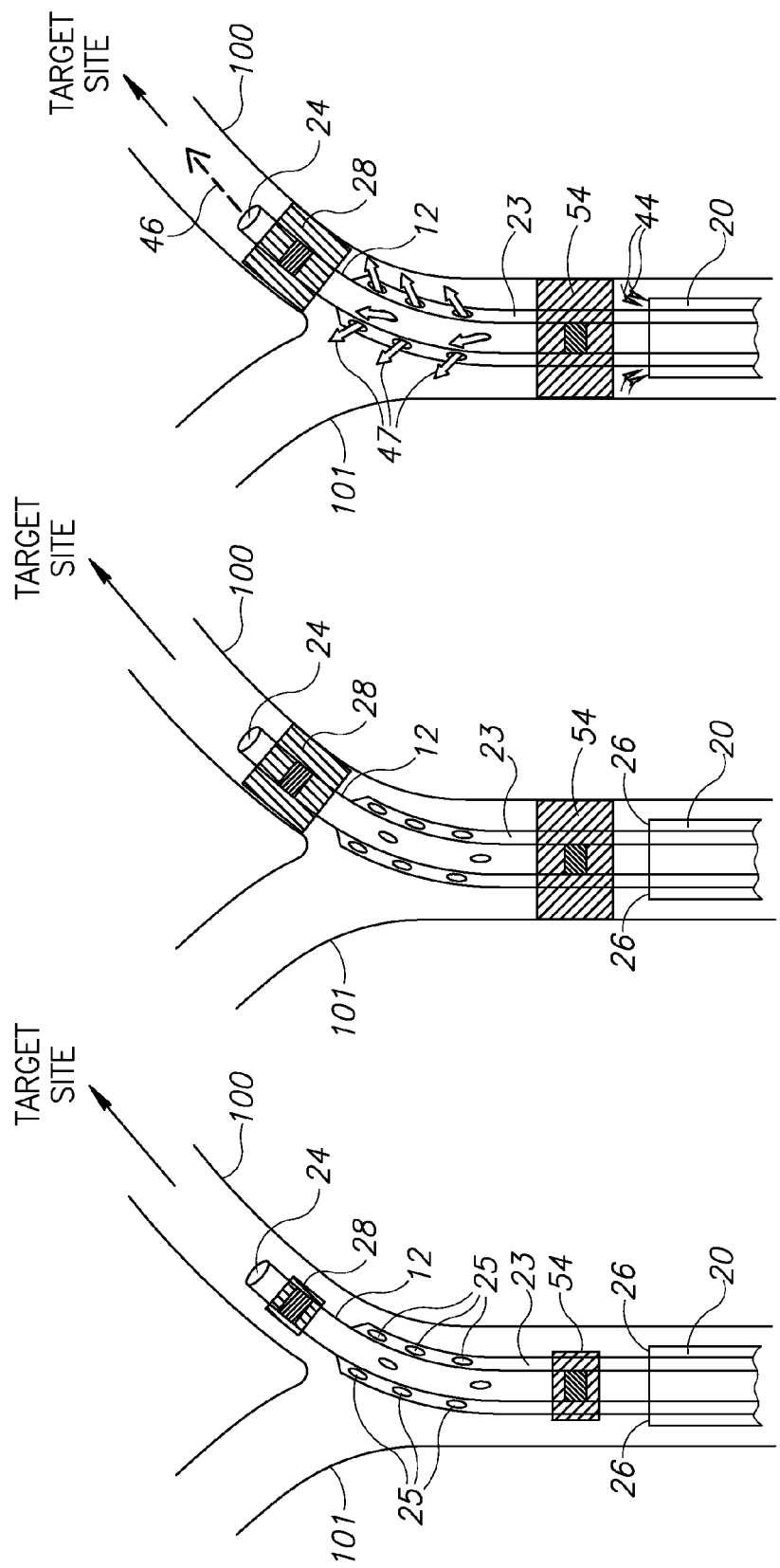

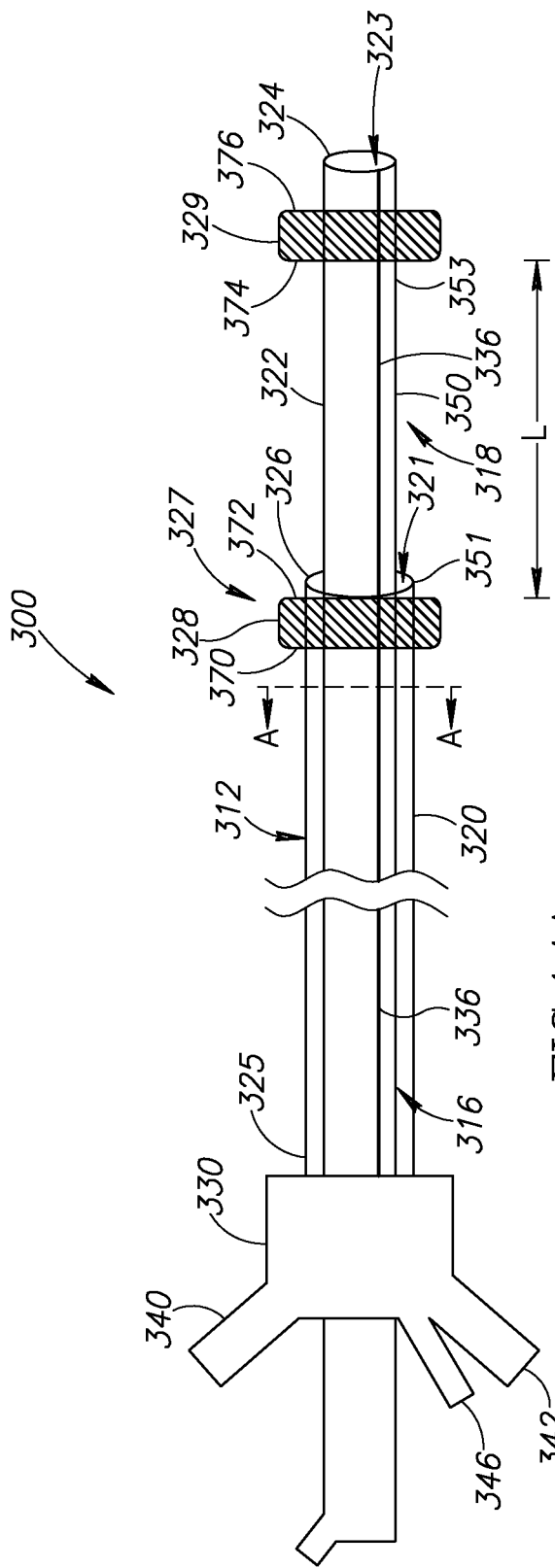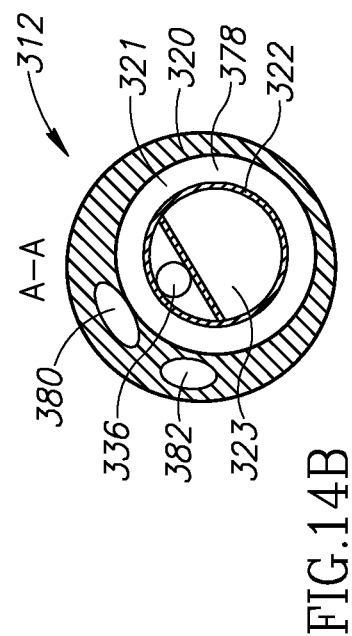
FIG.14A
FIG.14B

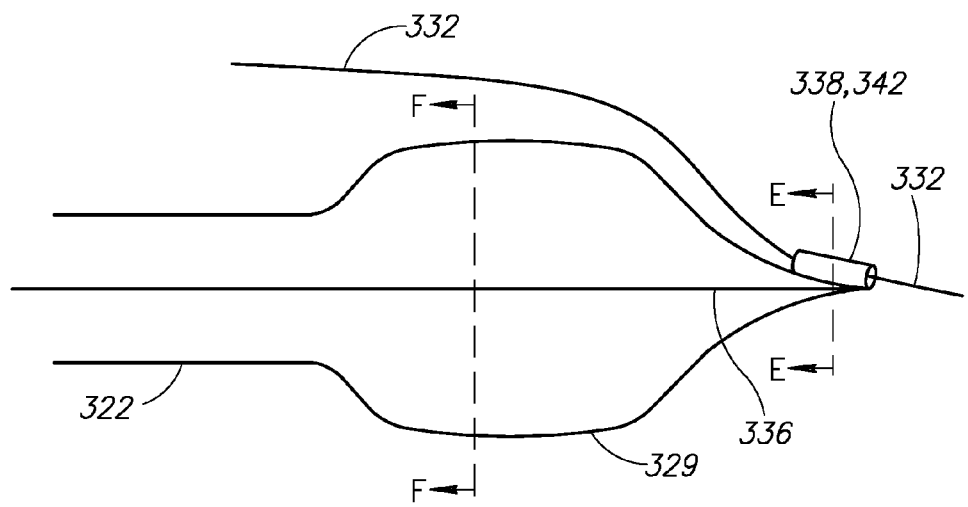
FIG.15D
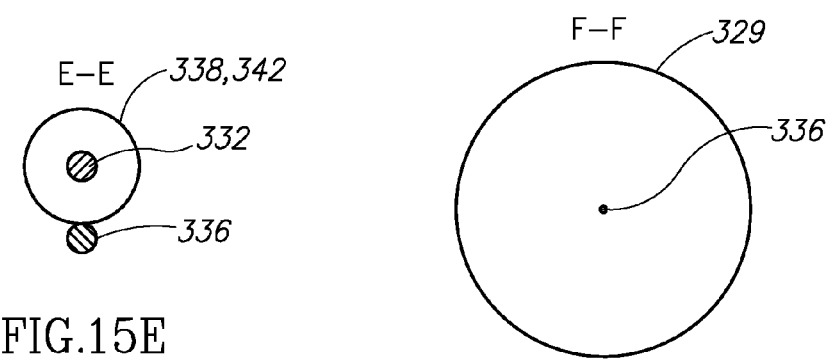
FIG.15E
FIG.15F

VARIABLE LENGTH CATHETER FOR DRUG DELIVERY

CROSS-REFERENCES TO RELATED APPLICATIONS

The present application is a continuation-in-part of U.S. patent application Ser. No. 13/080,667, filed on Apr. 6, 2011, which is a continuation-in-part of U.S. patent application Ser. No. 12/731,222, filed on Mar 25, 2010, now U.S. Pat. No. 8,109,897, issued on Feb. 7, 2012, which is a divisional of U.S. patent application Ser. No. 11/338,892,filed on Jan. 25, 2006, now U.S. Pat. No. 7,704,220, issued on Apr. 27, 2010, all of which are incorporated by reference herein in their entireties.

FIELD AND BACKGROUND OF THE INVENTION

The present invention relates to systems and methods for delivery of therapeutic or diagnostic agents, wherein the systems provide for varying lengths of the treatment area. The systems and methods herein are designed for selective treating of an area without adversely affecting other parts of the body.

Methods and devices designed to provide drugs to a vessel, include, for example, the use of drug coated balloons, such as disclosed in U.S. Pat. No. 5,954,706 to Sahatjian, for example. Such devices include a catheter with an expandable portion, wherein at least a portion of the exterior surface of the expandable portion is defined by a coating of hydrogel polymer. Incorporated within the hydrogel polymer is a solution of a preselected drug to be delivered to the tissue or plaque. Disadvantages of such devices include the need to choose a particular drug and dosage in advance, as well as limitations on the length and diameter of the treatment area as defined by the predetermined length and diameter of the expandable portion, since these devices often work by direct contact of the device to the vessel.

Another device is disclosed in U.S. Pat. No. 6,287,320 to Slepian. A catheter includes first and second expansile members which are expanded to occlude a diseased region, and a therapeutic agent is introduced into the diseased region via the catheter. The catheter is allowed to remain in place for a therapeutically effective amount of time to allow the therapeutic agent to contact the diseased portion for such a period of time.

Another device is disclosed in US Patent Publication 2007/0078433 to Schwager et al. This device includes a balloon catheter having a predetermined inflow angle of medication. A first and second balloon are positioned on the catheter, with a treatment zone therebetween. Disadvantages of devices such as the ones disclosed in the above-referenced publications include limitations on the length of the treatment area as predetermined by the distance between the expansile members.

A device disclosed in US Patent Application Publication Number 2005/0059930 to Garrison et al. includes a catheter system with at least two expandable occluding elements which are used to create a localized site for administration of agents. The catheters are slidable with respect to one another to vary the space between the balloons as desired. However, the localized site is prone to overpressure since there is no disclosed way to remove excess fluid from the site.

There is thus a need for, and it would be highly advantageous to have, a system and method for localized drug delivery within a vessel, with adjustability of the length of the treatment area and with means for reducing pressure buildup in the treatment zone.

SUMMARY OF THE INVENTION

There is provided, in accordance with embodiments of the present invention, a catheter system having an inner elongated element and an outer elongated element positioned coaxially with respect to the inner elongated element. The outer elongated element has a proximal end and a distal end, with an outer elongated element lumen extending from the proximal end to the distal end, and having an outlet port at the distal end. A proximal occlusion element is positioned at the distal end of the outer elongated element, proximal to the outlet port. The inner elongated element has a proximal end and a distal end, a blood-release element at the distal end of the inner elongated element, and a distal occlusion element positioned at the distal end of the inner elongated element. The distal end of the inner elongated element is distal to and movable with respect to the outer elongated element distal end. A core wire extends from the distal end to the proximal end of the inner elongated element. In accordance with further features of the present invention, the system may further include a treatment or diagnostic solution positioned within the outer elongated element lumen, between an outer wall of the inner elongated element and an inner wall of the outer elongated element and between the distal and proximal occlusion elements. Buildup of pressure by introduction of the solution can be prevented by blood flow through the blood-release element. The inner elongated element may further include a guidewire therethrough. A hub may be included at the outer elongated element proximal end, for introduction of a therapeutic or diagnostic solution into the outer elongated element lumen, and further for introducing inflation fluid to one or both of the occlusion elements. In some embodiments, the inner elongated element is introduced into the outer elongated element via the hub. The blood-release element may be included either as a separate distal element or as an opening within the distal occlusion element, wherein the blood-release element may be used for clearing blood out of the treatment zone, and additionally for introduction of a guidewire therethrough, for rapid exchange of catheters. In one embodiment the distal and proximal occlusion elements are inflatable balloons, and outer and inner elongated elements further comprise inflation lumens for inflating the inflatable balloons.

In accordance with further features of the present invention, the inner elongated element has an exposed portion, with an exposed portion proximal edge at a proximal occlusion element distal end, and an exposed portion distal edge at a distal occlusion element proximal end. The exposed portion has a length extending from the exposed portion proximal edge to the exposed portion distal edge, and this length may be varied by moving the inner elongated element with respect to the outer elongated element.

In accordance with an additional embodiment of the present invention, there is provided a method for treating a vessel. The method includes introducing an outer elongated element having a proximal occlusion element at a distal end thereof into the vessel, introducing an inner elongated element having a distal occlusion element and a blood-release element at a distal end thereof, positioning the outer elongated element coaxially with respect to the inner elongated element, and positioning a distal end of the inner elongated element distal to the distal end of the outer elongated element. The distal occlusion element is positionable at varying distances from the proximal occlusion element. The method further includes deploying the distal and proximal occlusion elements and introducing a treatment or diagnostic solution through the outer elongated element into the vessel between the distal and proximal occlusion elements while simultaneously removing blood from the vessel via the blood-release element.

In accordance with further features of the present invention, positioning of the outer elongated element coaxial to the inner elongated element may be done prior to introducing the outer and inner elongated elements into the vessel, or may be done during the introducing, wherein the inner elongated element may be introduced through the outer elongated element lumen, for example. The introducing into the vessel may be done by positioning the catheter over a guidewire positioned within the outer elongated element lumen, or by placing a guidewire through a blood-release element. The distance between the distal and proximal occlusion elements may be adjusted prior to introducing the drug solution.

In accordance with yet an additional embodiment of the present invention, there is provided a system having an outer elongated element with an outer elongated element proximal end and an outer elongated element distal end, the outer elongated element having an outer elongated element lumen extending from the outer elongated element proximal end to the outer elongated element distal end and having an outlet port at the outer elongated element distal end, and a proximal occlusion element located at the outer elongated element distal end, the proximal occlusion element proximal to the outlet port, an inner elongated element having an inner elongated element proximal end and an inner elongated element distal end, the inner elongated element having an inner elongated element lumen extending from the inner elongated element proximal end to the inner elongated element distal end, a blood-release element at the inner elongated element distal end, and a distal occlusion element located at the inner elongated element distal end. The inner elongated element is positioned within the outer elongated element lumen wherein the outer elongated element is coaxially arranged with respect to the inner elongated element, and wherein the inner elongated element distal end is distal to and movable with respect to the outer elongated element distal end. The system further may include a supply elongated element coaxial to the outer elongated element, the supply elongated element having an inlet port at a distal end thereof, wherein the inlet port is proximal to the outer elongated element distal end.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 5A-5C are illustrations of a catheter having a bendable distal end, in accordance with one embodiment of the present invention;

FIGS. 9A-9H are illustrations of the steps of a method of positioning a catheter in a vessel in accordance with additional embodiments of the present invention;

FIGS. 11A-11C are illustrations of the steps of a method for treating a specific target site in accordance with one embodiment of the present invention;

FIGS. 12A-12C are illustrations of a method for treating a specific target site in accordance with another embodiment of the present invention;

FIGS. 14A-14D are schematic and cross-sectional illustrations of a system in accordance with embodiments of the present invention, having an outer elongated element with a proximal occlusion element positioned thereon, an inner elongated element with a distal occlusion element positioned thereon, and at least one outlet port for delivery of a solution;

FIGS. 15A-15F are schematic and cross-sectional illustrations of the system of FIGS. 14A-14D, further including a blood-release element, in accordance with embodiments of the present invention;

DETAILED DESCRIPTION OF THE INVENTION

Figure 1A:
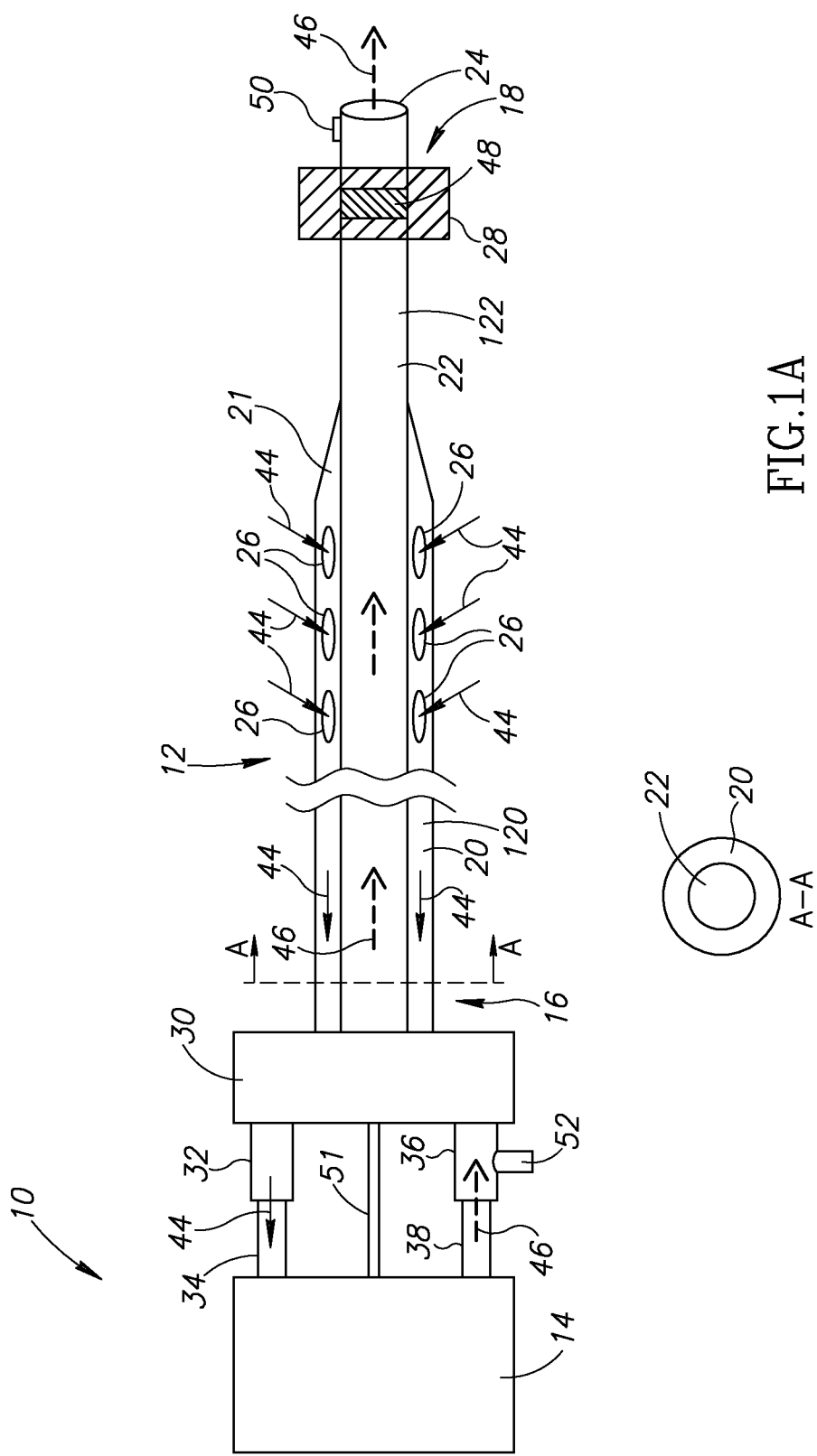
FIG. 1A is an illustration of a system including a catheter and a control unit, in accordance with one embodiment of the present invention.

The present invention is of systems and methods which can be used for delivery of a therapeutic or diagnostic agent into a vessel. For the purposes of the present invention, the term "delivery substance" is used to include any therapeutic or diagnostic agent which may be delivered into the vessel, including but not limited to medications, saline, contrast media, sealing agents, etc. The present invention can be used to selectively adjust the length of the vessel-access delivery portion of the catheter and to control the period of exposure of the delivery substance at the selected location in a contained manner.

The principles and operation of systems and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIGS. 14A and 14B, which are a schematic illustration and a cross-sectional illustration, respectively, of a system 300 in accordance with embodiments of the present invention. System 300 includes a catheter 312 which includes an outer elongated element 320 having an outer elongated element lumen 321 therethrough and an inner elongated element 322 having an inner elongated element lumen 323 therethrough. Inner elongated element 322 is preferably an elongated tubular member, extending through an entire length of catheter 312, having an inner elongated element proximal end 316 and an inner elongated element distal end 318. In some embodiments, inner elongated element 322 has a guidewire exit port 324 at or near inner elongated element distal end 318. Guidewire exit port 324 is configured for placement of a guidewire therethrough, as will be explained further hereinbelow, but can also be used for perfusion, or exchange of different sized guidewires, for example. In some embodiments, inner elongated element lumen 323 and guidewire exit port 324 are not included, and the profile of inner elongated element 322 may be reduced. Outer elongated element 320 is preferably an elongated tubular member having an outer elongated element proximal end 325 and an outer elongated element distal end 327. Outer elongated element 320 is positioned coaxially with respect to inner elongated element 322, as shown in cross-section A-A, in FIG. 14B, and extends from inner elongated element proximal end 316 to a location proximal to inner elongated element distal end 318.

In one embodiment, as shown in FIG. 14A, outer elongated element 320 has an outlet port 326 located at outer elongated element distal end 327. In this embodiment, outlet port 326 is created by the coaxial arrangement of outer elongated element 320 and inner elongated element 322, wherein an inner diameter of outer elongated element 320 is sized at least 0.10 mm (i.e. 0.004") greater than an outer diameter of inner elongated element 322 and may be 3 mm (0.12") greater or more, depending on the size of catheter 312. The space created by this difference in diameter creates a delivery lumen 378 (depicted in FIG. 14B) which is sufficiently sized for providing a delivery substance to the vessel, as will be described in greater detail hereinbelow. A distal end of delivery lumen 378 is outlet port 326. Moreover, delivery lumen 378 may be sized for placement of a guidewire therethrough, as will be explained. In embodiments of the present invention, an outer diameter of inner elongated element 322 is in a range of 0.02" to 0.08 inches, and more specifically may be in a range of 0.025-0.35" for a smaller version of system 300 or in a range of 0.05-0.06" for a larger version of system 300. An inner diameter of inner elongated element 322 is in a range of 0.01" to 0.05", and more specifically may be in a range of 0.015"-0.02" for a smaller version of system 300 and 0.035"-0.045" for a larger version of system 300. An outer diameter of outer elongated element 320 is in a range of 0.05"-0.15", and more specifically may be in a range of 0.055"-0.065" for a smaller version of system 300 and in a range of 0.115"-0.130" for a larger version of system 300. An inner diameter of outer elongated element 320 is in a range of 0.025"-0.1", and more specifically may be in a range of 0.030"-0.050" for a smaller version of system 300 and in a range of 0.080"-0.090" for a larger version of system 300. It should be readily apparent that the invention is not limited to the dimensions listed herein and that these dimensions should be taken as exemplary.

Figure 14C:
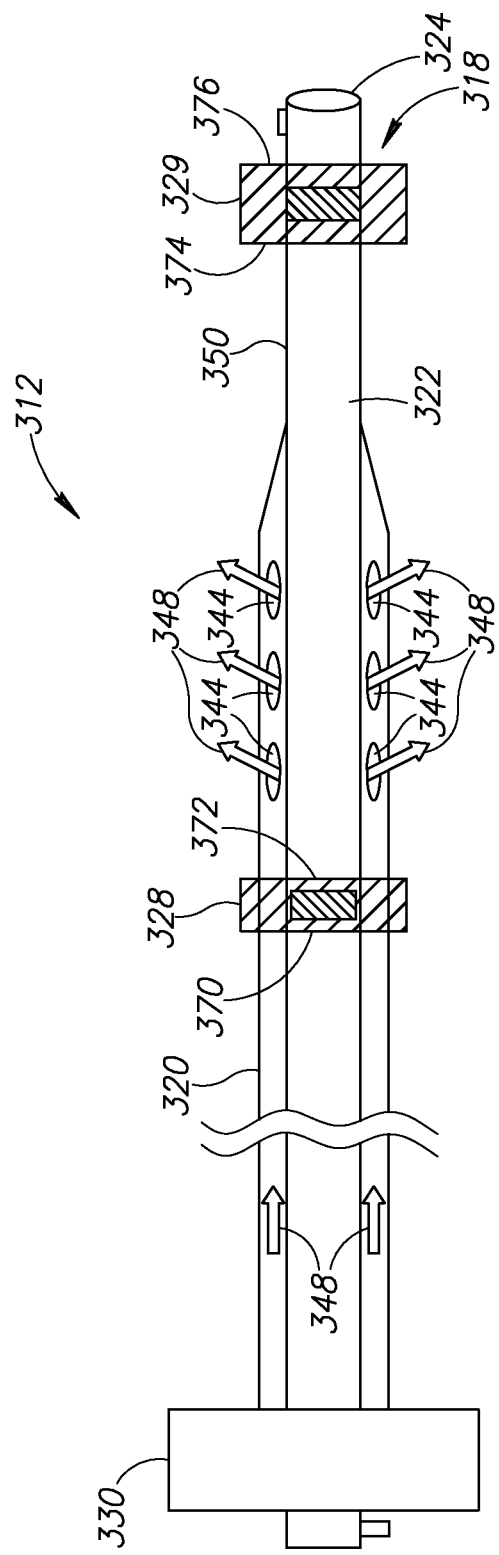
Figure 14D:
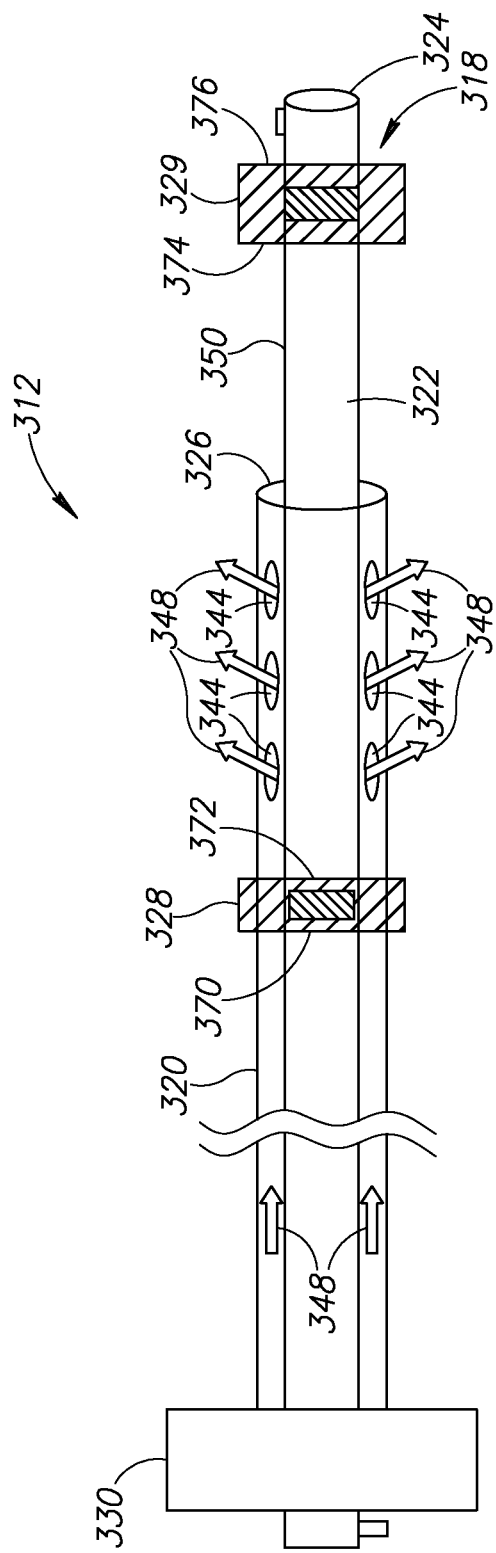

In another embodiment, as shown in FIG. 14C, outer elongated element 320 has multiple outlet ports 344, which are openings within a body of outer elongated element 320, at one or more locations along its length, for providing a delivery substance to the blood vessel. Outward movement of drug solution, contrast, diagnostic solution, or other substance is indicated by arrows 348. In yet another embodiment, as shown in FIG. 14D, both outlet port 326 and multiple outlet ports 344 are used.

Returning now to FIG. 14A, a proximal occlusion element 328 is positioned on outer elongated element 320 at or near outer elongated element distal end 327, such that proximal occlusion element 328 is proximal to outlet port 326. In the embodiments shown in FIGS. 14C and 14D, proximal occlusion element 328 is positioned proximal to multiple outlet ports 344. Proximal occlusion element 328 has a proximal occlusion element proximal end 370 and a proximal occlusion element distal end 372. A distal occlusion element 329 is positioned on inner elongated element 322, at or near inner elongated element distal end 318, proximal to guidewire exit port 324, and distal to outer elongated element distal end 327. Distal occlusion element 329 has a distal occlusion element proximal end 374 and a distal occlusion element distal end 376. Inner elongated element 322 is movable with respect to outer elongated element 320. Thus, an exposed portion 350 of catheter 312 may be defined as having an exposed portion proximal edge 351 at proximal occlusion element distal end 372 and an exposed portion distal edge 353 at distal occlusion element proximal end 374. Exposed portion 350 has a length L extending from exposed portion proximal edge 351 to exposed portion distal edge 353, and length L may be varied by moving inner elongated element 322 with respect to outer elongated element 322.

Inner elongated element lumen 323 may be configured to hold a guidewire therein, and outer elongated element lumen 321 is configured to hold inner elongated element 322 therein and to further hold a delivery substance in between an outer wall of inner elongated element 322 and an inner wall of outer elongated element 320 within delivery lumen 378. In some embodiments, outer elongated element lumen 321 is further configured to hold a guidewire therein. The delivery substance may be introduced into the vessel through outlet port 326 and/or multiple outlet ports 344, but is prevented from flowing outside of a treatment zone by inflation of proximal occlusion element 328 and inflation of distal occlusion element 329. Thus, a length of the treatment zone in the vessel is determined by length L of exposed portion 350.

A hub 330 is positioned at a proximal end of catheter 312 and is attached to outer elongated element 320 at outer elongated element proximal end 325. Hub 330 includes an infusion port 340 for introducing a delivery substance such as a drug solution into delivery lumen 378 (i.e. outer elongated element lumen 321) and a proximal occlusion element inflation port 342 for delivery of inflation fluid to proximal occlusion element 328. Hub 330 may further include a pressure monitoring valve 346.

Referring now to FIG. 14B, the configuration of outer elongated element 320 and inner elongated element 322 in accordance with embodiments of the present invention is shown in cross-section. Outer elongated element lumen 321 is configured to receive therein both inner elongated element 322 and a delivery substance introduced via infusion port 340. Outer elongated element 320 may further include an inflation lumen 380 for introducing inflation fluid into proximal occlusion element 328, and a pressure lumen 382. The pressure lumen has a proximal pressure transducer attached thereto which is capable of measuring the pressure of a column of fluid located within the pressure lumen. Outer elongated element lumen 321 may also be configured to receive a guidewire therethrough, in between the body of outer elongated element 320 and inner elongated element 322. Inner elongated element 322 may have an inner elongated element lumen 323 for receiving a guidewire therethrough, and further includes a distal inflation lumen for introducing inflation fluid into distal occlusion element 329. A core wire 336 is positioned within or attached to inner elongated element 322. In some embodiments, core wire 336 is positioned between layers of a polymer shaft of inner elongated element 322.

In some embodiments, outer elongated element 320 is advanced into a vessel first with a guidewire positioned through outer elongated element lumen 321, followed by inner elongated element 322 which may be advanced through outer elongated element lumen 321 of outer elongated element 320, resulting in the guidewire and inner elongated element 322 positioned side by side within outer elongated element lumen 321. In other embodiments, outer elongated element 320 and inner elongated element 322 are advanced together into the vessel. The introduction of system 300 with outer elongated element 320 and inner elongated element 322 may be done either as an over the wire system, wherein a guidewire is introduced into the vessel and then positioned within inner elongated element lumen 323, whereupon system 300 is advanced over the guidewire, or may be done using a blood-release element on inner elongated element 322, as will be described below with reference to FIGS. 15A-15F.

Figure 3:
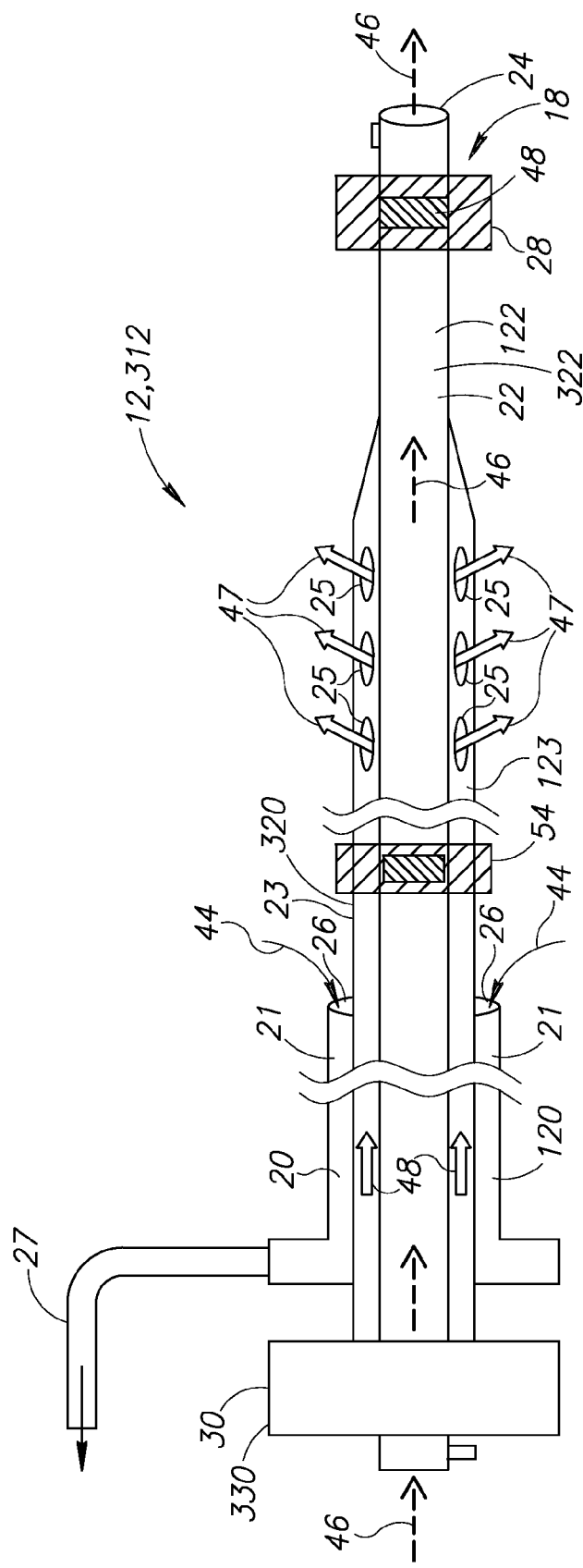
FIG. 3 is an illustration of a catheter in accordance with another embodiment of the present invention.

Reference is now made to FIG. 3, which is an illustration of a catheter 312 in accordance with another embodiment of the present invention. Catheter 312 is similar in construction to catheter 312 shown in FIGS. 14A-14D, with an additional feature of a supply elongated element 20 positioned coaxial to inner and outer elongated elements 322 and 320.

In one embodiment, supply elongated element 20 has inlet ports at one or more locations along its length for receiving blood from the blood vessel. In a preferred embodiment, as shown in FIG. 3, supply elongated element 20 has an inlet port 26 located at a distal end 21 thereof. In this embodiment, inlet port 26 is created by the coaxial arrangement of supply elongated element 20 and outer elongated element 320, wherein an inner diameter of supply elongated element 20 is sized at least 0.1 mm greater than an outer diameter of outer elongated element 320. The space created by this difference in diameter creates a port which is sufficiently sized for receiving supply blood from the vessel, as will be described in greater detail hereinbelow.

Hub 330 may connect supply elongated element 20 and inner elongated element 322 to a control unit, as described hereinbelow with reference to FIG. 2. The control unit may thermally alter (i.e. heat or cool) normothermic blood received from supply elongated element 20, and send the thermally altered blood out through inner elongated element 322. Blood received from supply elongated element 20 may be treated or altered in other ways as well, or may simply be used to perfuse the vessel distal to distal occlusion element 329.

In one embodiment, supply elongated element 20 is a standard vascular sheath and may have a side arm 27 from which blood is removed from the vessel and potentially sent to a control unit. In another embodiment, supply elongated element 20 is an extended sheath, and may extend to 100 cm or more depending on the application.

Reference is now made to FIGS. 15A-15F, which are schematic illustrations (FIGS. 15A and 15D) and cross-sectional illustrations (FIGS. 15B, 15C, 15E and 15F), respectively, of inner elongated element 322 with a blood-release element 338 in accordance with embodiments of the present invention. Blood-release element 338 may also be used for placement therethrough of a movable guidewire 332. Blood-release element 338 is sized with a diameter slightly larger than a diameter of movable guidewire 332. For example, an inner diameter of blood-release element 338 may be approximately 0.002" greater than a diameter of movable guidewire 332. This difference in diameter provides a clearance space for controlled removal of blood from the treatment zone, which can be useful in preventing pressure buildup in the treatment zone when the delivery substance is introduced. If sized correctly, delivery substance, such as contrast solution, should not be able to leak through the clearance space due to its viscosity being higher than that of blood.

Figure 15A:
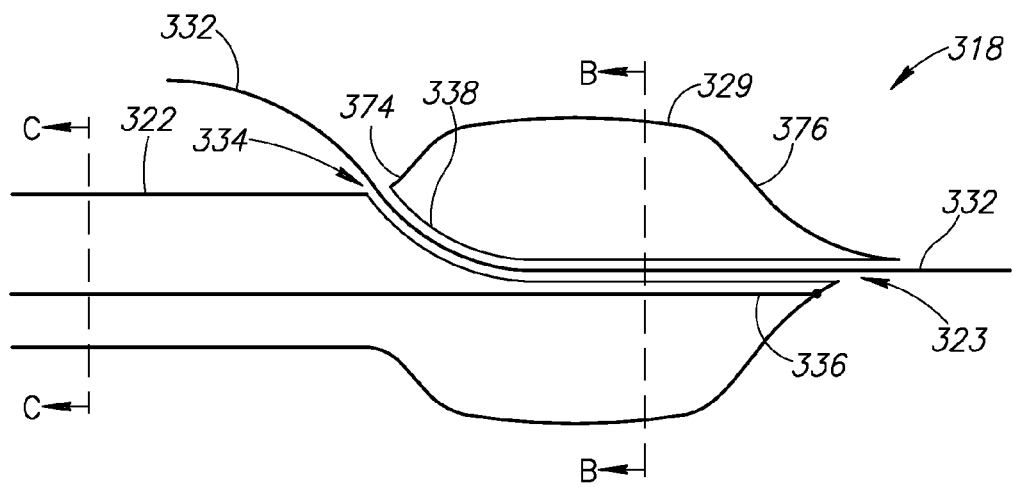
Figure 15B:
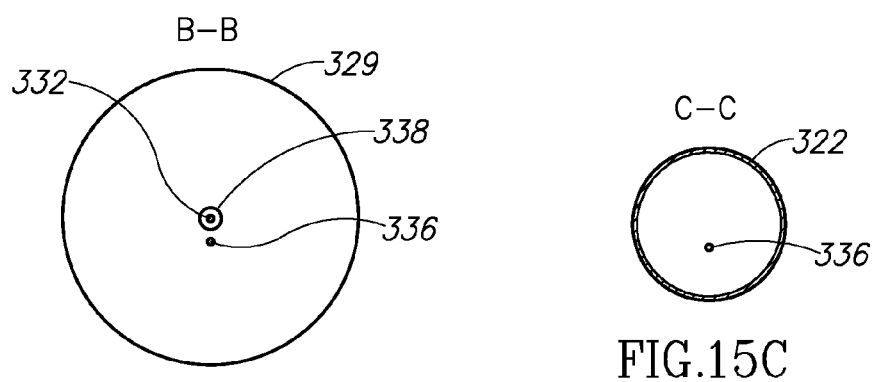
Figure 15C:
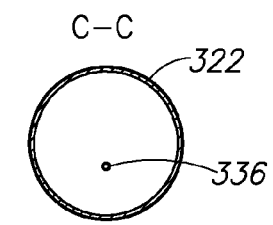
Figure 15G:
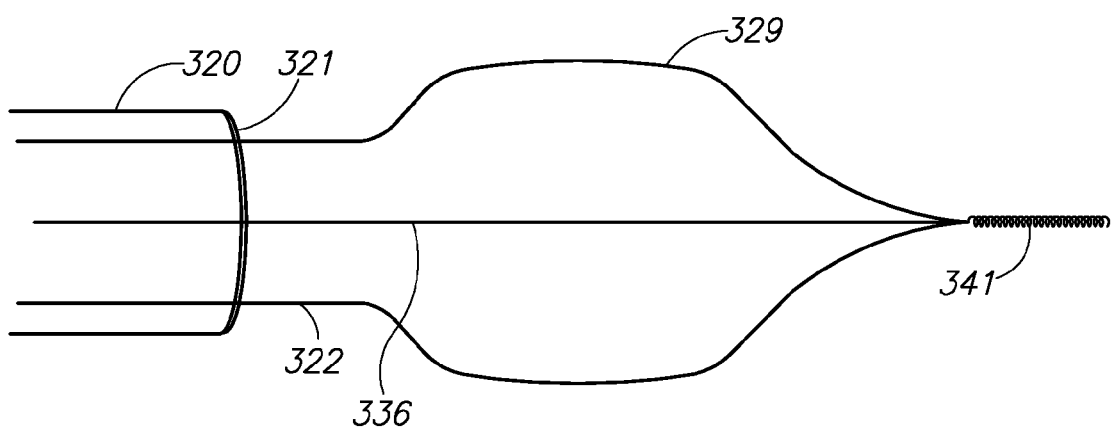
FIG. 15G is a schematic illustration of a catheter with a fixed wire balloon, in accordance with embodiments of the present invention.

In one embodiment, as shown in FIGS. 15A-15C, blood-release element 338 comprises an opening 334 at distal occlusion element proximal end 374. Movable guidewire 332 may be introduced into catheter 312 at inner elongated element distal end 318 through inner elongated element lumen 323 and exiting at opening 334 located at or near distal occlusion element proximal end 374. In another embodiment, as shown in FIGS. 15D-15F, blood-release element 338 comprises a separate distal element 342 positioned on inner elongated element 322 distal to distal occlusion element 329. In some embodiments, blood-release element 338 has a length of 4-20 cm. Blood-release element 338 allows for rapid exchange of catheters and for removal of blood from the treatment zone. Inner elongated element 322 further includes a core wire 336 positioned for providing stiffness through catheter 312. This enhances pushability of catheter 312. Core wire 336 is positioned within inner elongated element 322 and may be attached to distal occlusion element 329 at a distal end thereof and to proximal end 316 of inner elongated element 322. Core wire 336 may further be attached at additional points along the length of inner elongated element 322. In some embodiments, core wire 336 is sandwiched between polymeric layers of a shaft of inner elongated element 322.

For the embodiments shown in FIGS. 15A-15F wherein a blood-release element is used with movable guidewire 332, outer elongated element lumen 321 may house movable guidewire 332 when inner elongated element 322 and outer elongated element 320 are positioned coaxially to one another. In these embodiments, inner elongated element 322 and outer elongated element 320 may be initially positioned coaxial to one another, and movable guidewire 332 is introduced through blood-release element 338 of inner elongated element 322. Catheter 312, having both inner and outer elongated elements 322 and 320, is advanced over movable guidewire 332. Once movable guidewire 332 is positioned within blood-release element 338, it is further positioned in between an outer surface of inner elongated element 322 and an inner surface of outer elongated element 320—that is, within outer elongated element lumen 321. This allows for an over the wire type of advancement, but with a reduced profile, since an additional over the wire lumen is not required. In this case, inner elongated element lumen 323 may be eliminated thus reducing the profile of catheter 312. Alternatively, inner elongated element lumen 323 may be used for other items. For example, a mandrel may be introduced through inner elongated element lumen 323 for enhancing pushability and for advancing inner elongated element 322. In some embodiments, inner elongated element lumen 323 may be used for exchanging guidewires, or for putting a second guidewire in the vessel. Alternatively, inner elongated element lumen 323 may be used for perfusion. For example, in a case of prolonged occlusion while treating the vessel, blood may be introduced through inner elongated element lumen 323 to an area distal to distal occlusion element 329, thus making it possible to keep treating the vessel for as long as necessary. This may be particularly useful in the coronary arteries, for example, which cannot be occluded for a prolonged period of time. In some embodiments, blood may be cooled or otherwise treated and then introduced through inner elongated element lumen 323. In some embodiments, a supply element is included as well, as described with reference to FIG. 3, for removing blood from the vessel which may then be reintroduced through inner elongated element lumen 323. In some embodiments, inner elongated element 322 may be removed from outer elongated element 320 during a procedure.

Figure 16A:
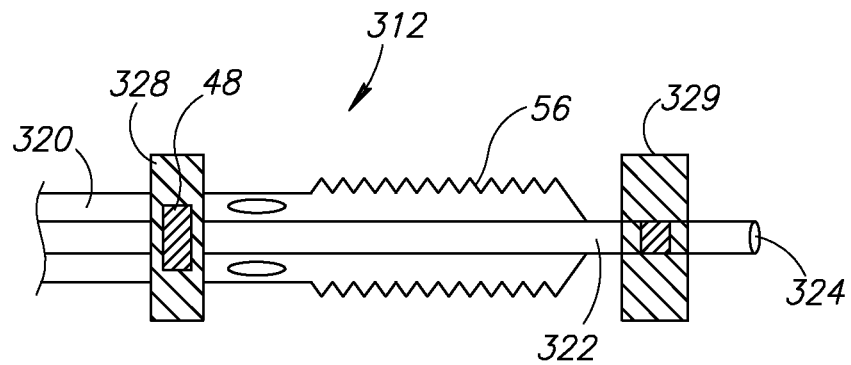
FIGS. 16A-16C are schematic illustrations of the system of FIGS. 14A-14D, showing a distal end thereof in accordance with embodiments of the present invention.
Figure 16B:
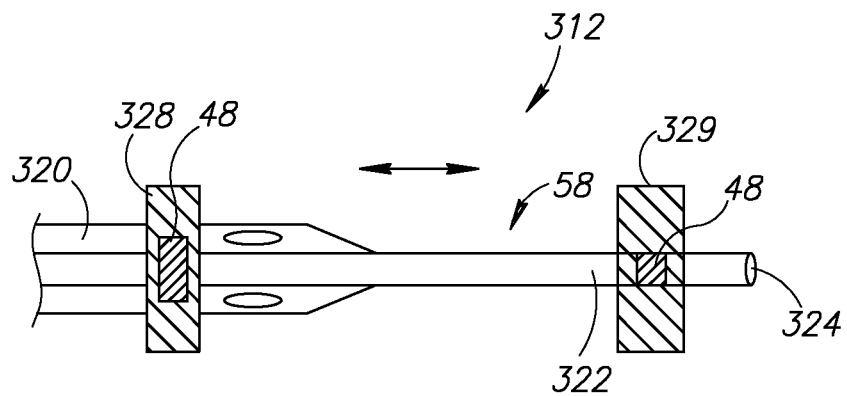
Figure 16C:
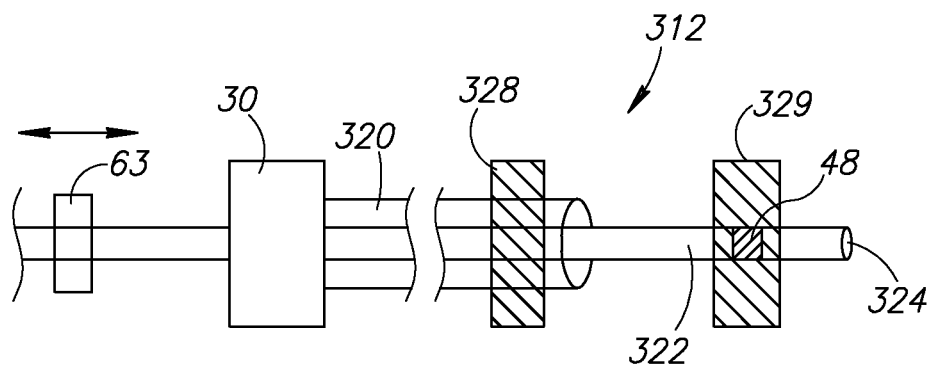

Reference is now made to 15G, which is an illustration of a catheter 312 in accordance with yet another embodiment. In this embodiment, instead of blood-release element 338, a fixed wire 341 is used. Thus, for example, distal occlusion element 329 may be a fixed wire balloon. In some embodiments, an additional movable wire may be introduced through outer elongated element lumen 321. In yet another embodiment, a blood-release element 338 and a fixed wire 341 are used, and blood-release element 338 is sized for blood to pass through but not for the drug solution Reference is now made to FIGS. 16A-16C, which are illustrations of a distal portion of catheter 312, in accordance with embodiments of the present invention, wherein distal occlusion element 329 is positionable at varying distances from proximal occlusion element 328. It should be noted that FIGS. 16A-16C are variations of FIGS. 4A-4C, described in further detail hereinbelow. Inner elongated element 322 is movable within outer elongated element 320. Movement can be a twisting motion, for example, wherein inner elongated element 322 and outer elongated element 320 are attached with a bellows 56, as shown in FIG. 16A. Alternatively, movement can be a sliding motion, wherein inner elongated element 322 and outer elongated element 320 are attached via telescoping means 58, as shown in FIG. 16B. In a preferred embodiment, movement is achieved by coaxial arrangement of outer elongated element 320 and inner elongated element 322, as shown in FIG. 16C. In this arrangement, it may be necessary to include an adjustable anchor 63 for anchoring the proximal portion of inner elongated element 322 to the body or surgical drape of the patient. Alternatively, a length of outer elongated element 320 may protrude proximal to the proximal end of catheter 312. In this case, it may be necessary to include an adjustable anchor for anchoring the proximal portion of outer elongated element 320 to the body or surgical drape of the patient. Any suitable adjustable anchor means may be used, including, for example, a luer lock, a gland, a squeeze-lock mechanism, etc. Any other means for changing a distance between distal occlusion element 329 and proximal occlusion element 328 or between distal end 318 of inner elongated element 322 and distal end 327 of outer elongated element 320 is included within the scope of the invention.

In embodiments of the present invention, radiopaque markers 48 may be included on distal occlusion element 329, proximal occlusion element 328 and other locations along catheter 312 for visualization of the position of catheter 312 within the vessel and relative positions of distal and proximal occlusion elements 329 and 328.

Reference is now made to FIGS. 17A-17F, which are schematic illustrations showing a method of using catheter 312.

Figure 17A:
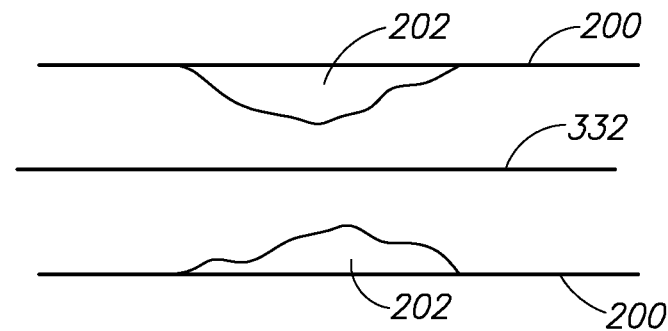
FIGS. 17A-17F are schematic illustrations of steps of a method of delivering a therapeutic or diagnostic agent to a treatment area of a vessel, in accordance with embodiments of the present invention.
Figure 17B:
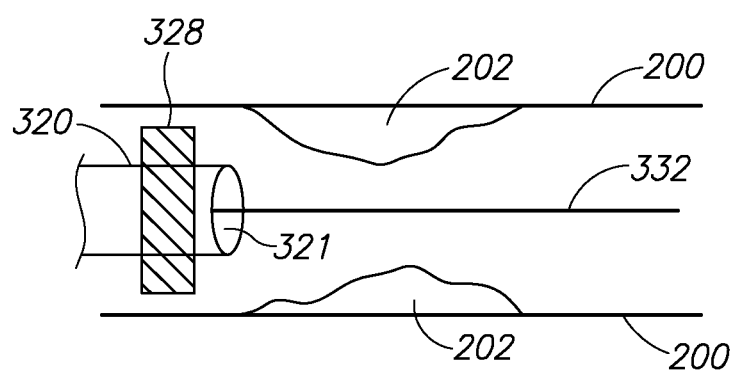
Figure 17C:
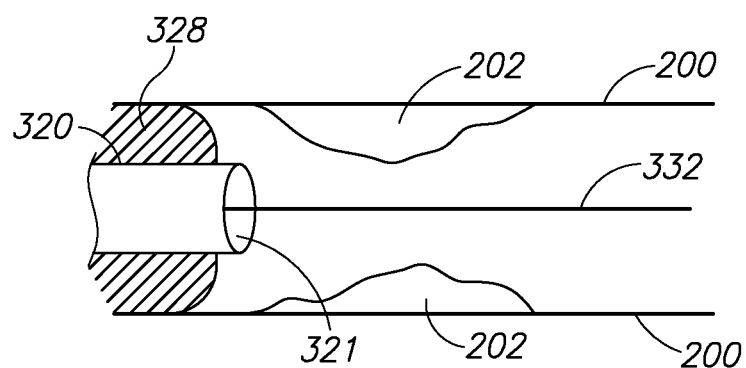
Figure 17D:
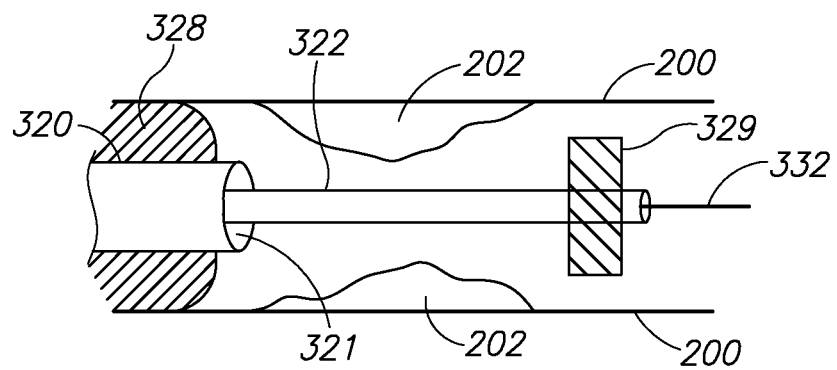
Figure 17E:
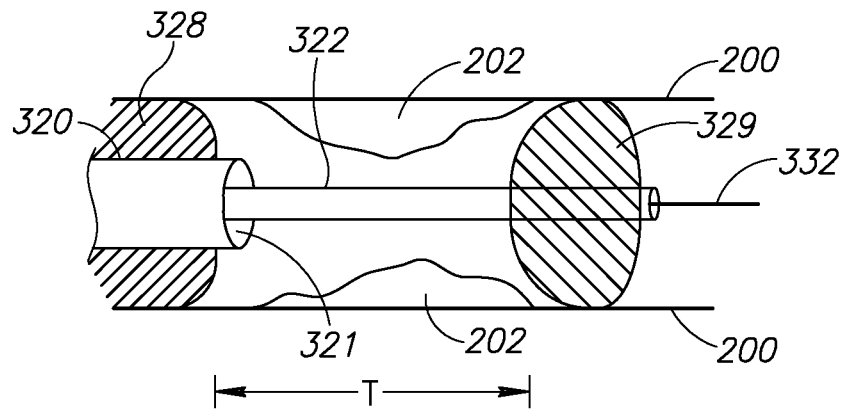
Figure 17F:
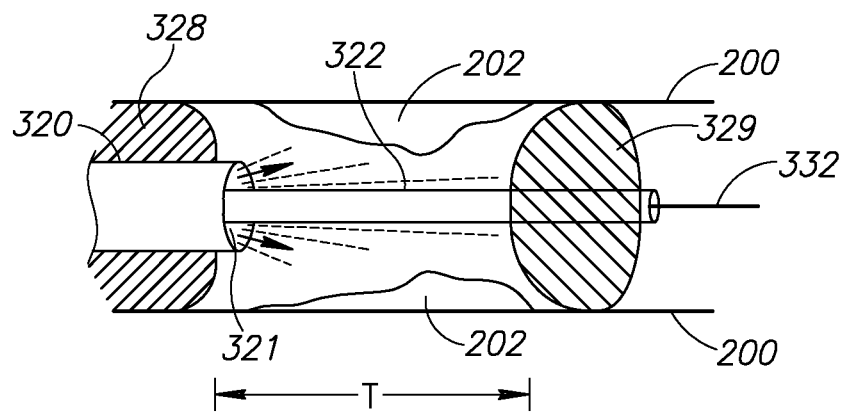

A vessel 200 is shown with a lesion 202. As shown in FIG. 17A, movable guidewire 332 is introduced into vessel 200 adjacent lesion 202. As shown in FIG. 17B, outer elongated element 320 is introduced over movable guidewire 332, and is positioned proximal to lesion 202. Next, as shown in FIG. 17C, proximal occlusion element 328 is inflated. In an alternative embodiment, proximal occlusion element 328 is inflated later on in the procedure, after inner elongated element 322 is in place. Next, as shown in FIG. 17D, inner elongated element 322 is introduced through outer 321 lumen of outer elongated element 320 and is positioned distal to lesion 202. Next, as shown in FIG. 17E, distal occlusion element 329 is inflated, thus defining a treatment area T between inflated proximal occlusion element 328 and inflated distal occlusion element 329. Next, as shown in FIG. 17F, a delivery substance, such as a drug solution, is introduced into treatment area T via outer elongated element lumen 321 of outer elongated element 320. It should be readily apparent that treatment area T may be adjusted by introducing inner elongated element 322 at varying distances from a distal end of outer elongated element 320. Alternatively or in addition to the embodiments shown herein, outer elongated element 320 may have one or multiple outlet ports 326, 344 as described with reference to FIGS. 14C and 14D. In some embodiments, the delivery substance may also be removed from vessel 200 through outlet port 326. In some embodiments, the method may include a repeatable cycle of introducing the delivery substance, removing the delivery substance, deflating distal and proximal occlusion elements, reestablishing blood flow, reinflating distal and proximal occlusion elements, and reintroducing the same or a different delivery substance. This cyclic introduction and removal of the delivery substance is possible since the delivery substance can remain inside outer elongated element 320, and distal and proximal occlusion elements may be inflated and deflated. This method can provide a benefit of prolonged drug exposure without prolonged stoppage of blood flow. In some embodiments, inner elongated element 322 may be removed from vessel 200 during the procedure, and a different catheter may be introduced through outer elongated element 320 for additional procedures.

Figure 18A:
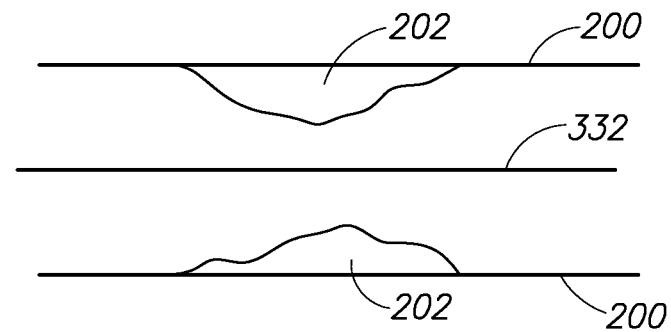
FIGS. 18A-18D are schematic illustrations of steps of a method of delivering a therapeutic or diagnostic agent to a treatment area of a vessel in accordance with additional embodiments of the present invention.
Figure 18B:
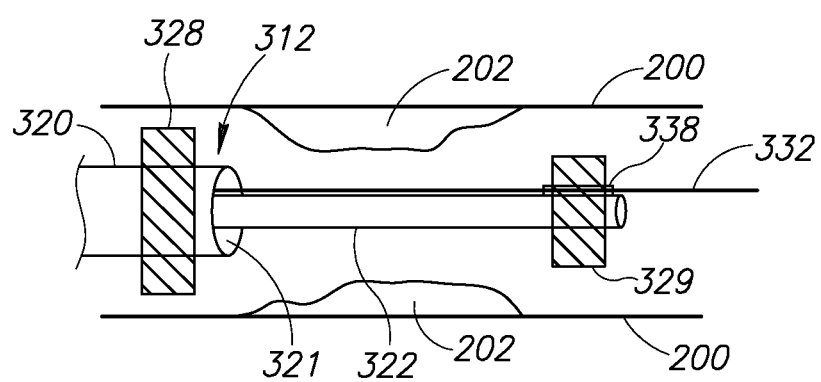
Figure 18C:
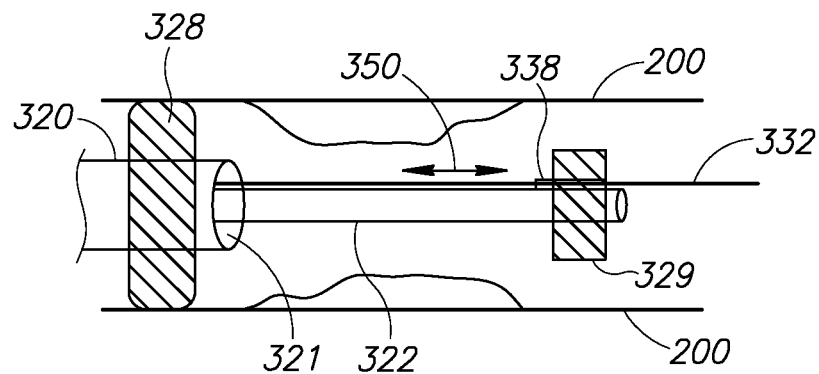
Figure 18D:
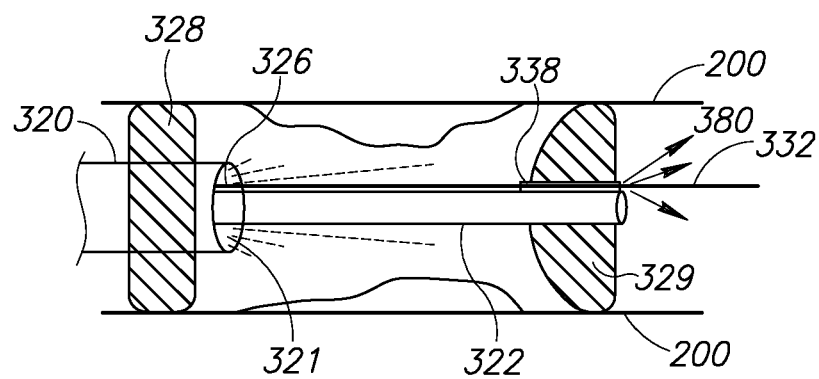

Reference is now made to FIGS. 18A-18D, which are schematic illustrations showing a method of using catheter 312 in accordance with additional embodiments of the present invention. A vessel 200 is shown with a lesion 202. As shown in FIG. 18A, movable guidewire 332 is introduced into vessel 200 adjacent lesion 202. Next, as shown in FIG. 18B, catheter 312 having inner elongated element 322 positioned within outer elongated element 320, is introduced over movable guidewire 332 by placing movable guidewire 332 through blood-release element 338 on inner elongated element 322. Movable guidewire 332 is further positioned proximally through outer elongated element lumen 321 of outer elongated element 320. Next, as shown in FIG. 18C, proximal occlusion element 328 is inflated, and inner elongated element 322 is adjusted, as shown by arrows 350, such that distal occlusion element 329 is positioned distal to lesion 202. Once inner elongated element 322 is in position, distal occlusion element 329 may be inflated, as shown in FIG. 18D. Blood may be allowed to leak out through blood-release element 338, as depicted by arrows 380, and a delivery substance, such as a drug solution, is introduced through outer elongated element lumen 321 of outer elongated element 320 through outlet port 326 and/or through multiple outlet ports 344 (not shown). Alternatively, the sequence of balloon inflation may be varied. For example, distal occlusion element 329 may be inflated first, followed by proximal occlusion element 328. It should be readily apparent that a feature of the present invention is the flexibility in inflating and/or deflating the occlusion elements as necessary. In some embodiments, the delivery substance may also be removed from vessel 200 through outlet port 326. In some embodiments, the method may include a repeatable cycle of introducing the delivery substance, removing the delivery substance, deflating distal and proximal occlusion elements, reestablishing blood flow, reinflating distal and proximal occlusion elements, and reintroducing the same or a different delivery substance. This cyclic introduction and removal of the delivery substance is possible since the delivery substance can remain inside outer elongated element 320, and distal and proximal occlusion elements may be inflated and deflated. This method can provide a benefit of prolonged drug exposure without prolonged stoppage of blood flow. In some embodiments, inner elongated element 322 may be removed from vessel 200 during the procedure, and a different catheter may be introduced through outer elongated element 320 for additional procedures.

Figure 19A:
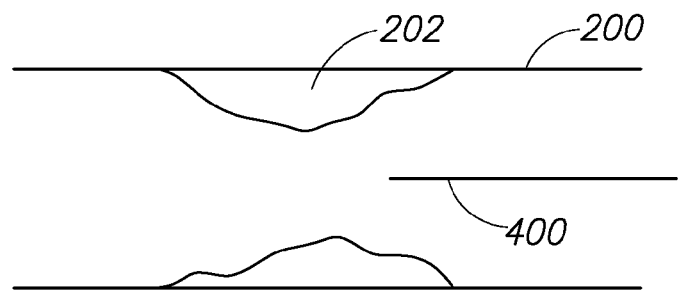
FIGS. 19A-19F are schematic illustrations of steps of a method of using a catheter in accordance with embodiments of the present invention for retrograde access of an artery such as a pedal artery, for example.
Figure 19B:
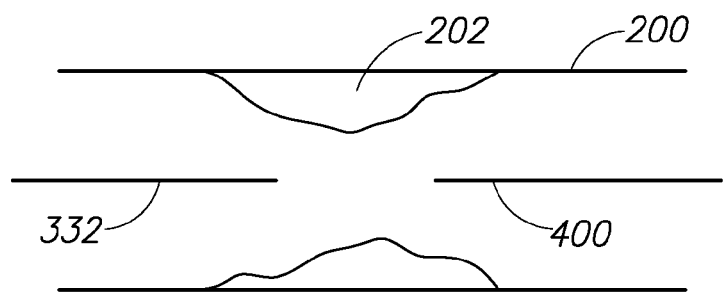
Figure 19C:
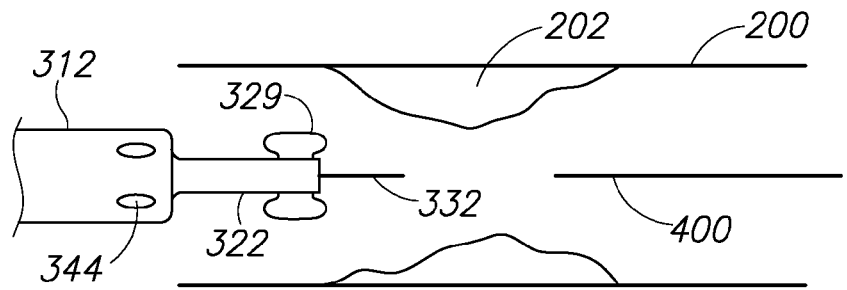
Figure 19D:
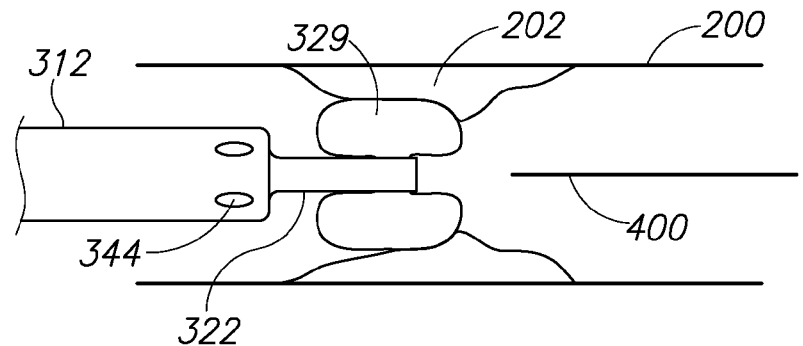
Figure 19E:
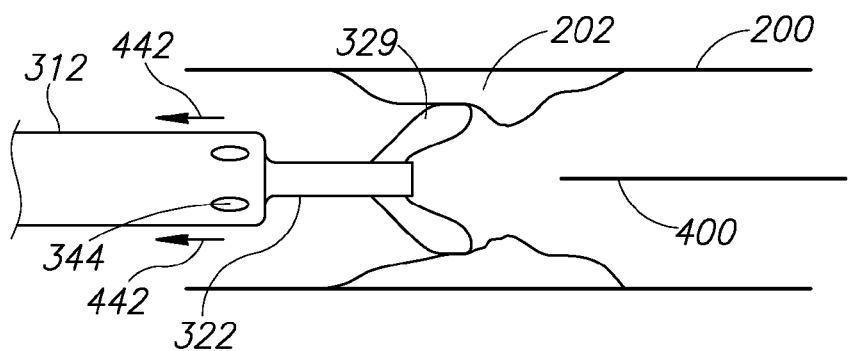
Figure 19F:
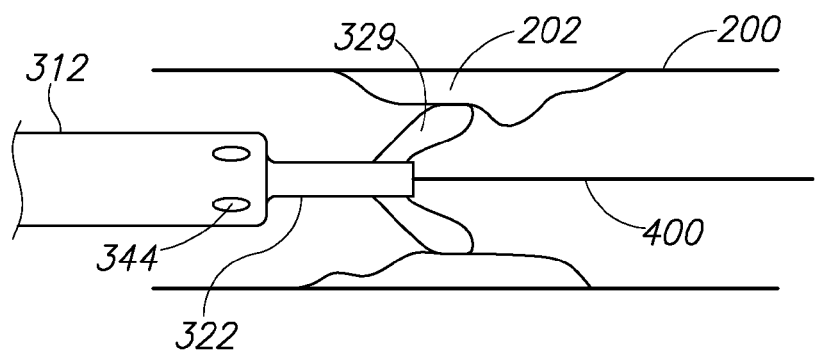

Reference is now made to FIGS. 19A-19F, which are schematic illustrations of a method of using catheter 312 for retrograde access of an artery such as a pedal artery, for example. In this embodiment, distal occlusion element 329 is a compliant balloon. As shown in FIG. 19A, first a retrograde guidewire 400 is advanced into a vessel 200 having an occlusion 202. Retrograde guidewire 400 is introduced into vessel 200 from a retrograde direction, via a hollow needle, for example. Next, a guidewire 332 is advanced into vessel 200 from an antegrade direction, as shown in FIG. 19B. Next, catheter 312 having distal occlusion element 329 on inner elongated element 322 is advanced over guidewire 332. In some embodiments, guidewire 332 is positioned through a lumen of inner elongated element 322. In other embodiments, guidewire 332 is positioned through a blood-release element, as described in embodiments of the present invention. In other embodiments, guidewire 332 is positioned through outer elongated element lumen 321. As described above, a delivery substance may be introduced through outlet ports 326, 344 during any point in the advancement of catheter 312 into vessel 200. When catheter 312 is in place on the antegrade side of occlusion 202, guidewire 332 is removed from catheter 312, and distal occlusion element 329 is expanded, as shown in FIG. 19D. Next, as shown in FIG. 19E, inner elongated element 322 (or all of catheter 312) is pulled back proximally, shown by arrows 442, and due to the compliant property of distal occlusion element 329, distal occlusion element 329 forms a funnel shape within the vessel 200 and/or within the occlusion 202. Next, as shown in FIG. 19F, retrograde guidewire 400 may be advanced through occlusion 202 and into inner elongated element 322 of catheter 312. Because of the funnel-shape of distal occlusion element 329, it is relatively easy to find the opening in inner elongated element 322. Retrograde guidewire 400 may be comprised of a flexible material and/or design (e.g. coil springs) so as not to puncture distal occlusion element 329. It should be readily apparent that guidewire 332 may alternatively be removed from catheter 312 just before advancement of retrograde guidewire 400. Once retrograde guidewire 400 is in catheter 312, retrograde guidewire 400 may be advanced proximally through catheter 312, and then used to replace guidewire 332 for the procedure to follow.

In alternative embodiments, a system is presented for use in delivering thermally treated blood to a location in the body.

Figure 1B:
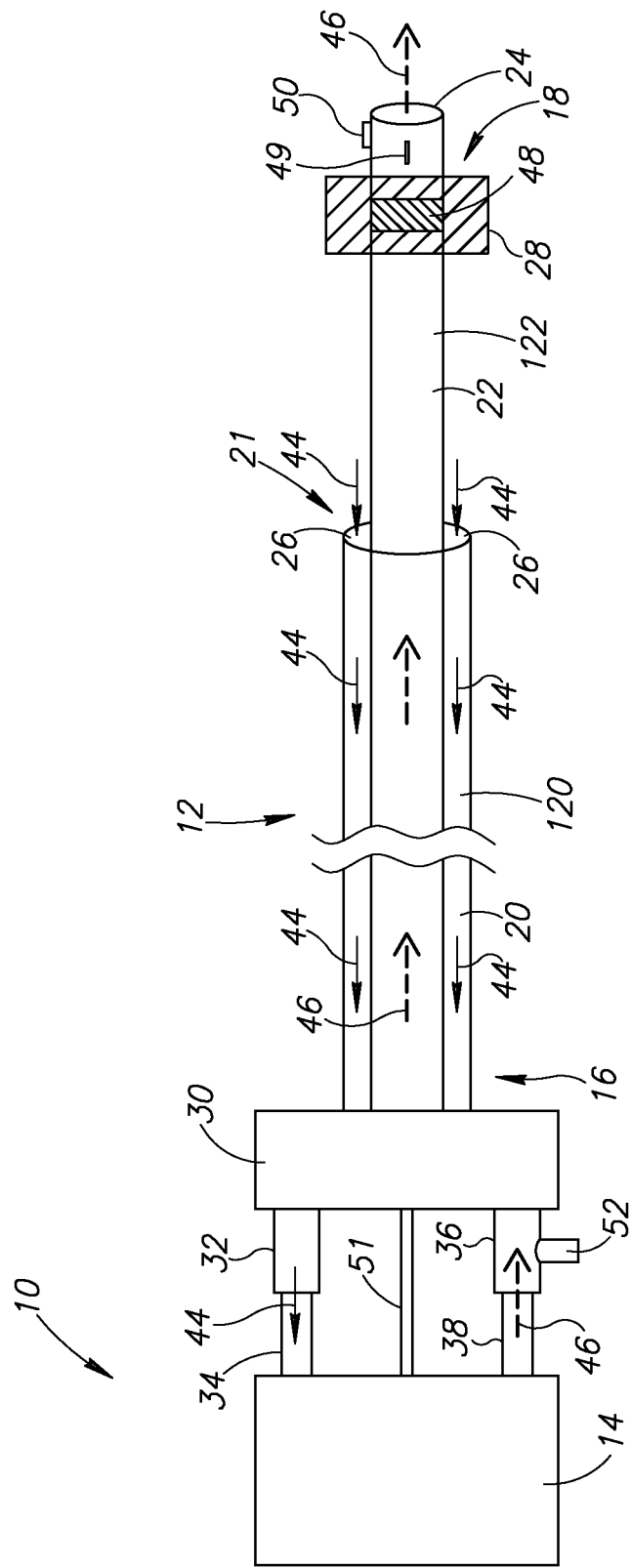
FIG. 1B is an illustration of a system including a catheter and a control unit, in accordance with another embodiment of the present invention.

Referring now to the drawings, FIGS. 1A and 1B illustrate a system 10 for selective cooling or heating of an organ, in accordance with preferred embodiments of the present invention. System 10 includes a catheter 12 and a control unit 14. Catheter 12 has a proximal end 16 and a distal end 18, and includes a supply elongated element 20 having a supply lumen 120 therethrough and a delivery elongated element 22 having a delivery lumen 122 therethrough. Delivery elongated element 22 is preferably an elongated tubular member, extending through an entire length of catheter 12, from proximal end 16 to distal end 18, and has an exit port 24 at or near distal end 18 for delivery of blood to a target site. Supply elongated element 20 is preferably an elongated tubular member which is positioned coaxially with respect to delivery elongated element 22, as shown in cross-section A-A, and extends from proximal end 16 of catheter 12 to an area proximal to distal end 18. In an alternative embodiment, supply elongated element 20 runs alongside delivery elongated element 22. In one embodiment, as shown in FIG. 1A, supply elongated element 20 has inlet ports 26 at one or more locations along its length, for receiving normothermic blood from the blood vessel. In a preferred embodiment, as shown in FIG. 1B, supply elongated element 20 has an inlet port 26 located at a distal end 21 thereof. In this embodiment, inlet port 26 is created by the coaxial arrangement of supply elongated element 20 and delivery elongated element 22, wherein an inner diameter of supply elongated element 20 is sized at least 0.1 mm greater than an outer diameter of delivery elongated element 22. The space created by this difference in diameter creates a port which is sufficiently sized for receiving supply blood from the vessel, as will be described in greater detail hereinbelow. In a preferred embodiment, an outer diameter of delivery elongated element 22 is in a range of 0.081 inches to 0.128 inches and an inner diameter of supply elongated element 20 is in a range of 0.100 inches to 0.162 inches.

As shown in FIGS. 1A and 1B, at least one occlusion element 28 is positioned at or near distal end 18 of catheter 12, proximal to exit port 24 and distal to a distal end 21 of supply elongated element 20. A hub 30 for connecting supply elongated element 20 and delivery elongated element 22 to control unit 14 is located at proximal end 16 of catheter 12. Hub 30 includes an inlet connector 32 for providing supply blood to a supply blood inlet 34 in control unit 14, and an outlet connector 36 for receiving delivery blood from a delivery blood outlet 38 in control unit 14. Control unit 14 thermally alters (i.e. heats or cools) normothermic blood received from supply blood inlet 34, and sends the thermally altered blood out through delivery blood outlet 38. Catheter 12 can be introduced over a guidewire, either as an over-the-wire system or as a rapid exchange system, or may include a fixed wire at its distal tip. In a preferred embodiment, delivery elongated element 22 acts as a guidewire lumen as well. In alternative embodiments, a separate guidewire lumen is positioned alongside or coaxial with delivery elongated element 22. In the fixed-wire configuration, catheter 12 could further include a torqueable catheter shaft. In one embodiment, such as the one depicted in FIG. 1B, delivery elongated element 22 and supply elongated element 20 are detachable from and/or movable with respect to one another.

The general cycle of blood flow is as follows. Normothermic blood, depicted by unbroken arrows 44, flows from a blood vessel, through at least one inlet port 26, and into supply elongated element 20. Supply elongated element 20 delivers the normothermic blood to control unit 14 via inlet connector 32. Blood is then thermally altered in control unit 14. Delivery elongated element 22 receives thermally altered blood, depicted by broken arrows 46, from delivery blood outlet 38 in control unit 14 via outlet connector 36, and delivers the thermally altered blood to the target site in the body. In order to ensure that heating or cooling of the target site is accomplished without causing heating or cooling of other parts of the body, it is necessary to physically separate the collection of normothermic blood from the delivery of thermally altered blood. In order to accomplish this separation using a single device, catheter 12 is designed with both a supply elongated element and a delivery elongated element having an occlusion element 28 for separation of blood inflow and outflow. By placing occlusion element 28 between distal end 21 of supply elongated element 20 and exit port 24, only the blood proximal to occlusion element 28 enters supply lumen 120, and the thermally altered blood only reaches that part of the arterial system which is distal to occlusion element 28.

Figure 2:
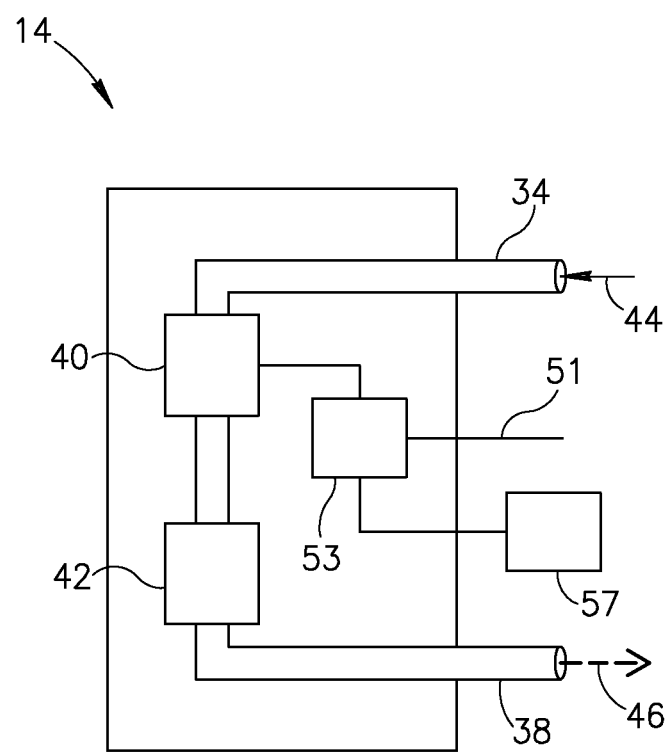
FIG. 2 is a schematic illustration of the control unit of the systems of FIGS. 1A and 1B.

Reference is now made to FIG. 2, which is a schematic illustration of control unit 14 in greater detail. Control unit 14 includes supply blood inlet 34 for receiving normothermic blood, depicted by unbroken arrow 44, and delivery blood outlet 38 for delivering thermally altered blood, depicted by broken arrow 46. Control unit 14 further includes a thermal adjustor 40 for changing a temperature of normothermic blood received from supply blood inlet 34, thus producing thermally altered blood. Thermal adjustor 40 can be a heating mechanism, a cooling mechanism, or a combination heating/cooling mechanism which is controllable by a user. In a preferred embodiment, thermal adjustor 40 is a cooling mechanism such as, for example, Medtronic, Inc.'s Bio-Cal® Blood Temperature Control Module or the MYOthermXP® Cardioplegia System. Alternatively, thermal adjustor 40 comprises a coiled tubing in an ice bath. In a preferred embodiment, control unit 14 further includes a pumping mechanism 42 to facilitate delivery of thermally altered blood through delivery blood outlet 38. Pumping mechanism 42 can be, for example, a centrifugal blood pump (Bio-Pump®, Medtronic, Inc.; Sarns™Centrifugal System, Terumo Cardiovascular Systems) or an electromagnetic pump (Levitronix® CentriMag® Blood Pumping System, Levitronix GmbH). In one embodiment, control unit 14 further comprises a vacuum to assist in withdrawal of the normothermic blood.

In order to more closely monitor physiological parameters during a procedure, sensors 50 may be placed at or near exit port 24, shown schematically in FIGS. 1A and 1B. Sensors 50 can include one or several sensors, capable of measuring pressure, temperature, flow, or a combination thereof. In an alternative embodiment, pressure is measured by providing an additional lumen referred to as a pressure lumen. The pressure lumen has a proximal pressure transducer attached thereto which is capable of measuring the pressure of a column of fluid located within the pressure lumen. Sensors 50 are in communication with control unit 14 via conventional wires 51 or via wireless communication. As shown in FIG. 2, control unit 14 can further include a processor 53 for receiving and processing signals from sensors 50 and providing an output based on the processed signals. Output can be sent to a display 57, which provides output information to a user. The user can make a decision based on this output information regarding further adjustments of the temperature, flow and pressure. Display 57 can be, for example, a visual, audio, numeric or any other suitable display. When a user sees the display, he/she can manually adjust thermal adjustor 40. The user can also decide to immediately stop the procedure if necessary. Alternatively, processor 53 sends output directly to thermal adjustor 40, which then automatically changes cooling or heating parameters based on the output.

In one embodiment, hub 30 further includes an infusion port 52, as shown in FIGS. 1A and 1B. Infusion port 52 can be used, for example, to introduce contrast media to the site. Alternatively, infusion port 52 can be used to introduce drugs. For example, lytic agents which are typically used to dissolve clots can be introduced via infusion port 52 into an artery, rather than the common practice of intravenous delivery of these agents. Alternatively, in some circumstances it may be desirable to introduce clotting agents, which can be done via infusion port 52. It should be readily apparent that any suitable agent, compound, drug, or substance can be introduced via infusion port 52, and all of these possibilities are included within the scope of the present invention.

Occlusion element 28 is comprised of an atraumatic surface so as not to damage the inner walls of a blood vessel. In a preferred embodiment, occlusion element 28 has a hydrophilic surface, which by attracting water forms a natural atraumatic layer. Furthermore, a hydrophilic surface can provide means for occlusion which is configured to open when in contact with water components from the blood. Occlusion element 28 may further include a coating for providing long-term (measured in hours, days or even months) implantation of catheter 12 in the body. Alternatively or in addition, occlusion element 28 may further include a drug coating. In one embodiment, occlusion element 28 is a balloon, such as is commonly used with catheter systems, and is expandable by introduction of a fluid therein, wherein the fluid can be a liquid or a gas. In this embodiment, a separate inflation lumen is included within catheter 12, either alongside or coaxial with delivery elongated element 22, and is in fluid communication with occlusion element 28. Fluid is introduced via an inflation port (not shown) positioned at hub 30. These types of balloons and inflation lumens are commonly known in the art. The balloon may be elastomeric, compliant, semi-compliant or non-compliant, as long as it serves to occlude the vessel without causing damage to the internal walls. In one embodiment, the balloon is pre-formed and relatively thin, so as to reduce the pressure necessary to inflate the balloon, while keeping the outer diameter to a minimum. For example, balloon thickness may range from 0.0001 inches to 0.001 inches, a range which is smaller than thicknesses of standard occlusion balloons.

In another embodiment, occlusion element 28 is a self-expanding element confined within a retractable sheath, such that upon retraction of the sheath, the self expanding element expands to a diameter sufficient to occlude the vessel. In this embodiment, the sheath is connected to a retractor positioned at proximal end 16 of catheter 12. The self-expanding element may be comprised of an elastic or spring-like material, or a shape-memory alloy. Such materials are known in the art. In another embodiment, occlusion element 28 is a mechanically actuated mechanism, whereby it is expanded by mechanical means. In yet another embodiment, occlusion element 28 is comprised of a temperature sensitive material which can be expanded or retracted by exposure to specific temperatures. Specifically, perfusion of cooled or heated blood through delivery lumen 122 would cause expansion of occlusion element 28, and perfusion of normothermic blood through delivery lumen 122 (such as, for example, during renormalization of temperature) would cause retraction of occlusion element 28. This may be accomplished, for example, by using a shape-memory material, either as occlusion element 28 itself, or as an actuator positioned alongside occlusion element 28. Similarly, this could be accomplished by using a bi-metallic strip. In one embodiment, occlusion element 28 is an integral part of the catheter, wherein a portion of catheter 12 having a slightly wider diameter is configured to be wedged into the vessel, and thus acts as occlusion element 28, providing both occlusion and anchoring functionality.

Occlusion element 28 further includes a radiopaque marker 48 for viewing of a location of catheter 12 generally and occlusion element 28 specifically within the vessel. In one embodiment, occlusion element 28 is itself comprised of radiopaque material. In alternative embodiments, one or more radiopaque markers 48 are positioned on occlusion element 28. Additional radiopaque markers 48 may also be positioned in other places along catheter 12 such as, for example, at distal end 18, or at inlet ports 26. In one embodiment, a radiopaque marker 48 is positioned at the distal tip of catheter 12. Radiopaque marker 48 can be a ring surrounding the distal tip, or, in order to minimize stiffness at the tip, a radiopaque marker 49 (shown in FIG. 1B) may be comprised of a small sliver of radiopaque material embedded within a portion of the distal tip. In one embodiment, radiopaque marker 48 is filled with an adhesive and positioned so as to seal an inflation lumen for inflation of occlusion element 28.

Reference is now made to FIG. 3, which is an illustration of a catheter 12 in accordance with another embodiment of the present invention. Catheter 12 is similar in construction to catheter 12 shown in FIGS. 1A and 1B, with an additional feature of an auxiliary delivery elongated element 23, preferably situated between supply elongated element 20 and delivery elongated element 22. Auxiliary delivery elongated element 23 is preferably an elongated tubular member having an auxiliary lumen 123 therethrough, and is configured to receive a supplemental blood flow from control unit 14 (shown in FIGS. 1A and 1B) and to deliver the supplemental blood (depicted by wide arrows 47) to a vessel. In one embodiment, the supplemental blood is taken from the control unit 14 and introduced into auxiliary delivery elongated element 23 at an initial thermally altered temperature. Supplemental blood as depicted by wide arrows 47 undergoes a temperature change during its flow from the proximal end to the distal end of auxiliary delivery elongated element due to conduction from the normothermic blood in the blood vessel which is in close proximity thereto. In this embodiment, the temperature of supplemental blood that exits ports 25 of auxiliary delivery elongated element 23 is of a different temperature $T_2$ than the temperature $T_1$ of the thermally altered blood depicted by broken arrows 46, which is delivered to the target site. The presence of an additional layer of blood flow in a lumen surrounding delivery elongated element 22 provides increased insulation for the thermally altered blood being delivered to the target site. Furthermore, blood from auxiliary delivery elongated element 23 can be used for simultaneous treatment of different parts of the body. Thus, for example, if it were desired to treat the target site with one temperature and an additional site with another temperature, auxiliary delivery elongated element 23 could be used for treatment of the additional site. The amount of temperature change that occurs within auxiliary delivery lumen 123 depends on the flow rate and the initial temperature difference between the thermally altered blood entering auxiliary delivery lumen 123 and the normothermic blood surrounding auxiliary delivery elongated element 23.

In a preferred embodiment, auxiliary delivery elongated element 23 is coaxially arranged with respect to delivery elongated element 22, and includes at least one secondary exit port 25, preferably in a distal portion thereof. In an alternative embodiment, exit port 25 is configured similar to inlet port 26 as depicted in FIG. 1B, wherein an exit port 25 is created by the coaxial arrangement of auxiliary delivery elongated element 23 and delivery elongated element 22, wherein an inner diameter of auxiliary delivery elongated element 23 is sized at least 0.1 mm greater than an outer diameter of delivery elongated element 22. The space created by this difference in diameter is sufficient for delivering supply blood to the vessel. The distal portion of auxiliary delivery elongated element 23 is proximal to exit port 24. Supply elongated element 20 is positioned coaxially with respect to auxiliary delivery elongated element 23, and distal end 21 of supply elongated element 20 is proximal to secondary exit ports 25. In one embodiment, supply elongated element 20 is a standard vascular sheath and may have a side arm 27 from which normothermic blood is sent to control unit 14. In another embodiment, supply elongated element 20 is an extended sheath, and may extend to 100 cm or more depending on the application.

A second occlusion element 54 may be positioned proximal to secondary exit ports 25 and distal to inlet ports 26 of supply elongated element 20. In this way, a first target site is supplied by thermally altered blood exiting delivery elongated element 22 and having a temperature $T_1$, and a second target site is separately supplied by supplemental blood exiting auxiliary delivery elongated element 23 and having a temperature $T_2$.

Figure 4A:
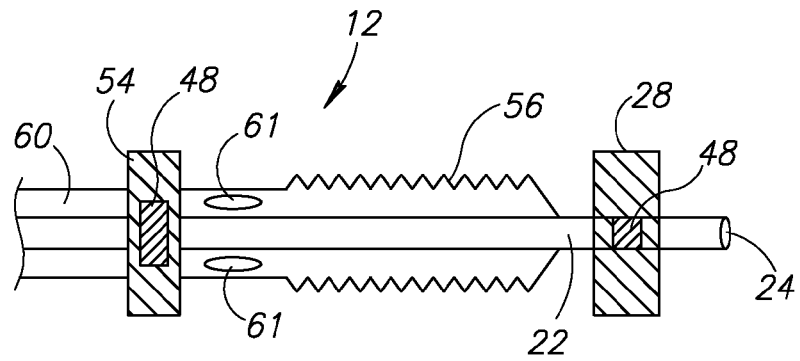
FIGS. 4A, 4B and 4C are illustrations of several embodiments of a distal portion of the catheters of FIG. 1A, FIG. 1B and FIG. 3, having distal ends which are variably positionable.
Figure 4B:
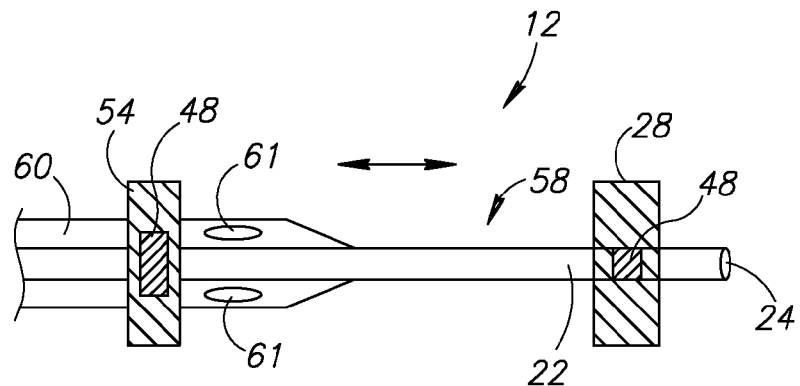
Figure 4C:
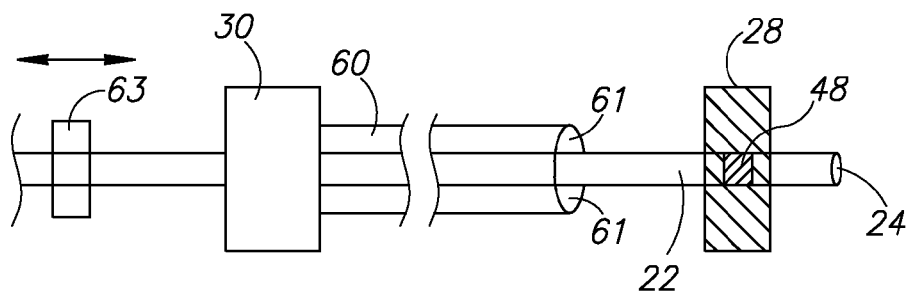

Reference is now made to FIGS. 4A-4C, which are illustrations of a distal portion of catheter 12, in accordance with another embodiment of the present invention, wherein exit port 24 is positionable at varying distances from ports 61. Ports 61 are inlet or outlet ports of a coaxial elongated element 60, which can be any elongated element coaxial to delivery elongated element 22. In one embodiment, coaxial elongated element 60 is a supply elongated element and ports 61 are inlet ports. In another embodiment, coaxial elongated element 60 is an auxiliary delivery elongated element, and ports 61 are secondary exit ports. Delivery elongated element 22 is movable within coaxial elongated element 60. Movement can be a twisting motion, for example, wherein delivery elongated element 22 and coaxial elongated element 60 are attached with a bellows 56, as shown in FIG. 4A. Alternatively, movement can be a sliding motion, wherein delivery elongated element 22 and coaxial elongated element 60 are attached via telescoping means 58, as shown in FIG. 4B. In a preferred embodiment, movement is achieved by coaxial arrangement of coaxial elongated element 60 and delivery elongated element 22, as shown in FIG. 4C. In this arrangement, delivery elongated element 22 can be variably positioned within coaxial elongated element 20. Thus, a length of delivery elongated element 22 may protrude proximal to the proximal end of catheter 12. In this case, it may be necessary to include an adjustable anchor 63 for anchoring the proximal portion of delivery elongated element 22 to the body or surgical drape of the patient. Alternatively, a length of supply elongated element 20 may protrude proximal to the proximal end of catheter 12. In this case, it may be necessary to include an adjustable anchor for anchoring the proximal portion of supply elongated element 20 to the body or surgical drape of the patient. These configurations allow for the tip of catheter 12 to be positioned as desired, without concern for the resulting location of the proximal end. Any suitable adjustable anchor means may be used, including, for example, a luer lock, a gland, a squeeze-lock mechanism, etc. Any other means for changing a distance between exit port 24 and ports 61 is included within the scope of the invention.

In some instances, it may be desirable to anchor catheter 12 into a vessel, providing greater control and easier accessibility to the target site. Reference is now made to FIGS. 5A-5C, which are illustrations of a catheter having a bendable distal end 18 for anchoring. As shown in FIG. 5A, catheter 12 includes delivery elongated element 22 and occlusion element 28. At least one exit port 24 is located distal to occlusion element 28. In one embodiment, exit port 24 is at distal end 18 of catheter 12. In another embodiment, exit port 24 is located anywhere between occlusion element 28 and distal end 18. In one embodiment, distal end 18 is initially in a straightened positioned as it is advanced over a guidewire 62. Guidewire 62 is insertable through delivery lumen 122. Alternatively, guidewire 62 may be insertable through a separate guidewire lumen (not shown), which is either coaxial with or adjacent to delivery lumen 122. Catheter 12 is advanced over guidewire 62 until a desired location is reached. Guidewire 62 is then removed, allowing catheter 12 to assume a bent configuration, as depicted in FIG. 5B. The bent configuration is suitable for anchoring in a vessel, as shown schematically in FIG. 5C. In an alternative embodiment, catheter 12 has a fixed wire at its distal end, and distal end 18 is initially straightened by inserting a removable stylet. Once the desired location is reached, the stylet is removed, causing distal end 18 to assume its bent configuration. In one embodiment, distal end 18 is comprised of a shape memory alloy.

Alternatively, it may be desirable to anchor catheter 12 in a vessel other than the one leading to the target site. For example, if catheter 12 is anchored in a branch vessel, thermally altered blood can be diverted into the main vessel by strategically placing exit port 24 at a specific location or locations.

Figure 6:
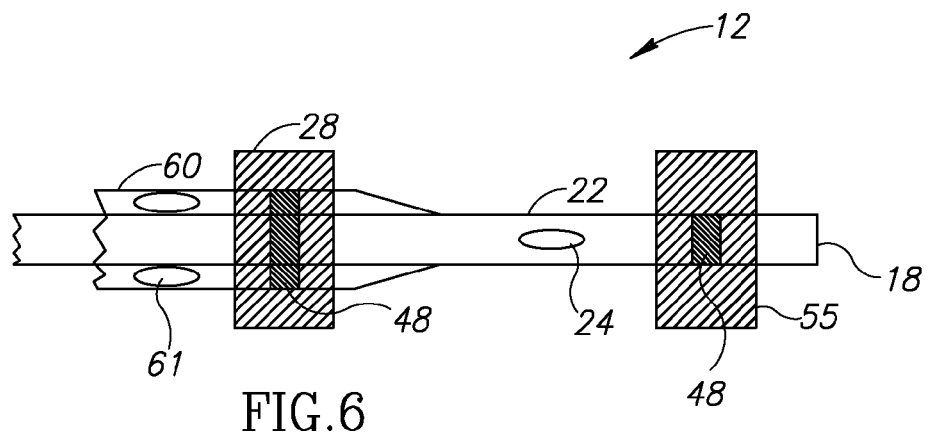
FIG. 6 is an illustration of a catheter which is suitable for anchoring in a separate vessel in accordance with one embodiment of the present invention.

Reference is now made to FIG. 6, which is an illustration of catheter 12 suitable for anchoring in a separate vessel, in accordance with one embodiment of the present invention. Catheter 12 has a closed distal end 18 and an exit port 24 located along its shaft, proximal to distal end 18. Catheter 12 further includes at least two occlusion elements: first occlusion element 28, which is positioned between exit port 24 and ports 61 of coaxial elongated element 60, and distal occlusion element 55, which is positioned between exit port 24 and distal end 18 of catheter 12. Coaxial elongated element 60 and ports 61 can be supply elongated element 20 with inlet ports 26, or auxiliary delivery elongated element 23 and secondary exit ports 25. First occlusion element 28 is designed to separate an area for receiving thermally altered blood (i.e. the target site) from an area supplying normothermic blood to control unit 14, or from an area receiving supplemental blood at a different temperature $T_2$. Distal occlusion element 55 is designed to act as an anchor, while also separating an area for receiving thermally altered blood (the target site) from an untreated area. In a preferred embodiment, first and distal occlusion elements 28 and 55 include radiopaque markers 48 for allowing for positioning of catheter 12 within the blood vessel.

Figure 7A:
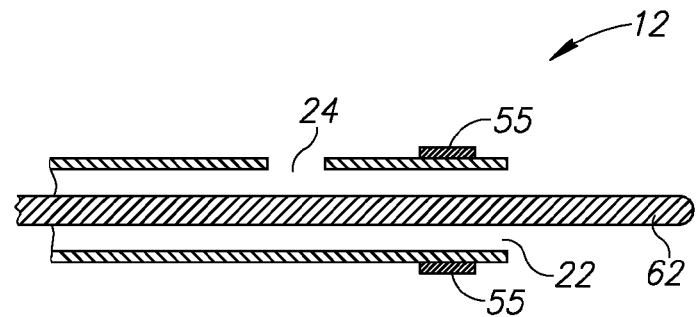
FIGS. 7A-7C are illustrations of a distal portion of a catheter which is suitable for anchoring in a separate vessel, in accordance with another embodiment of the present invention.
Figure 7B:
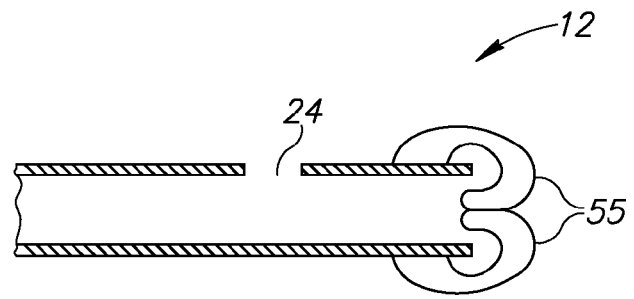
Figure 7C:
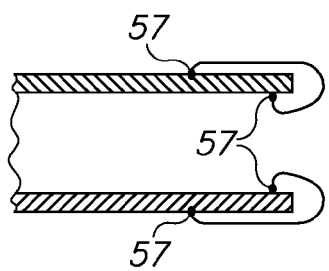

Reference is now made to FIGS. 7A and 7B, which are illustrations of a distal portion of catheter 12, suitable for anchoring in a separate vessel, in accordance with another embodiment of the present invention. As shown in FIG. 7A, guidewire 62 is introducible through delivery elongated element 22. In an alternative embodiment, catheter 12 includes a separate guidewire elongated element (not shown) either coaxial with or alongside delivery elongated element 22. Catheter 12 includes a distal occlusion element 55, which in one embodiment is an inflatable balloon designed to extend over distal end 18 upon inflation. As shown in FIG. 7B, inflation of distal occlusion element 55 results in expansion of the balloon over distal end 18, causing the delivery lumen to be sealed. This type of configuration can be accomplished, for example, by attaching the balloon to the catheter shaft near the distal end of the catheter, such that upon inflation, the balloon is configured to expand over the edge of catheter 12. Alternatively, distal occlusion element 55 can have multiple attachment points 57, as shown in FIG. 7C in a deflated state, which dictate a direction of expansion for distal occlusion element 55. Exit port 24 is located on the shaft of catheter 12, and is positioned proximal to distal occlusion element 55.

It should be readily apparent that in all of the described embodiments, additional lumens may be included for various purposes. For example, a lumen for oxygenation of blood may be added. Additional cooling/heating lumens or additional lumens to control flow or pressure may be added as well.

In a preferred embodiment, system 10 is used to provide hypothermia for treatment of stroke. A target temperature for cooling is in the range of 18 to 30 degrees Celsius, and may be maintained for hours or days. The system described herein also allows for gradual rewarming of the treated area by slowly introducing blood of different temperatures.

Figure 8C:
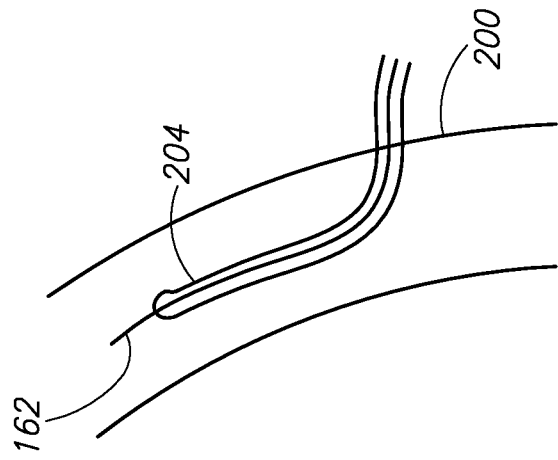
FIGS. 8A-8H are illustrations of the steps of a method of positioning a catheter in a vessel in accordance with embodiments of the present invention.
Figure 8B:
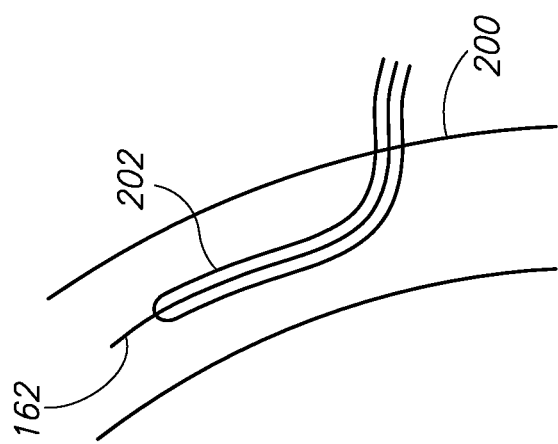
Figure 8A:
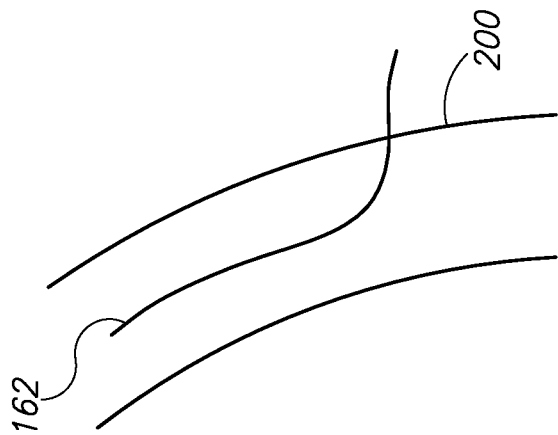
Figure 8F:
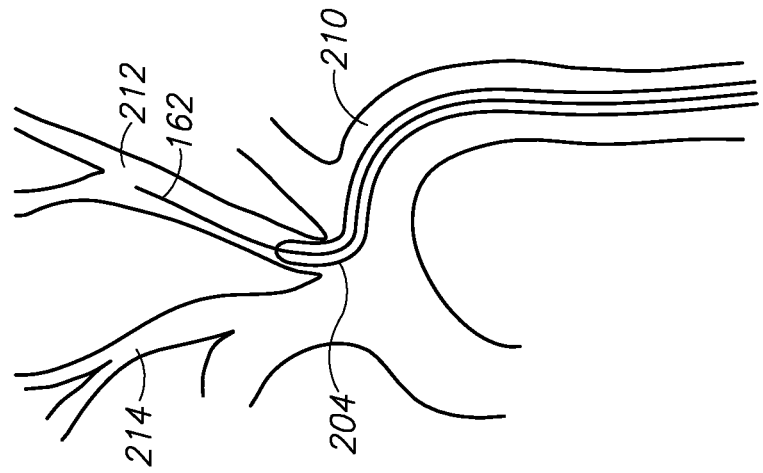
Figure 8E:
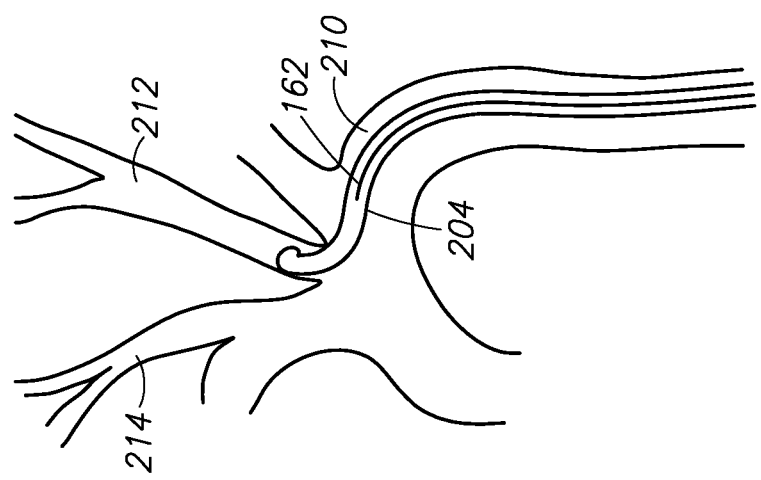
Figure 8D:
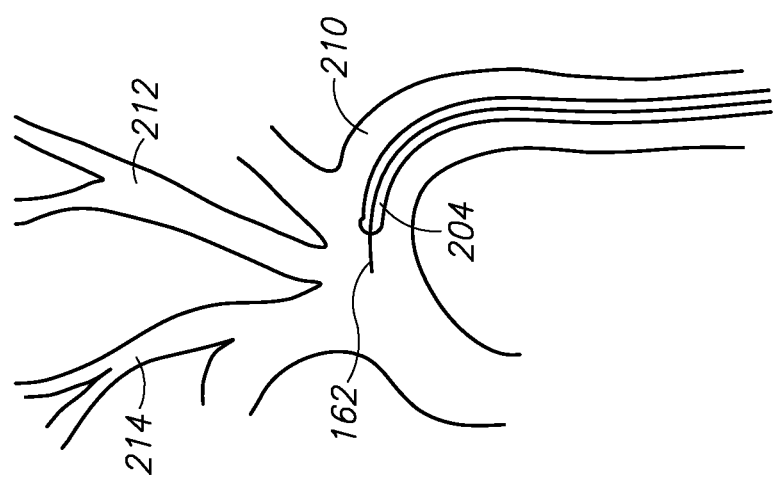
Figure 8H:
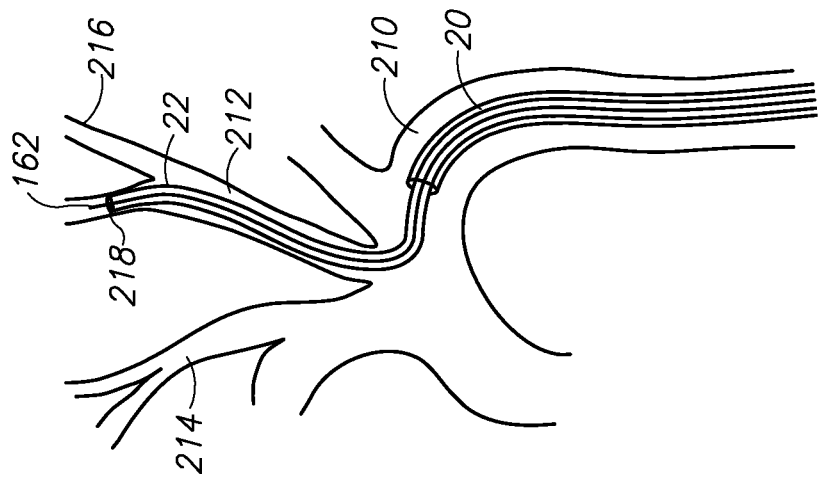
Figure 8G:
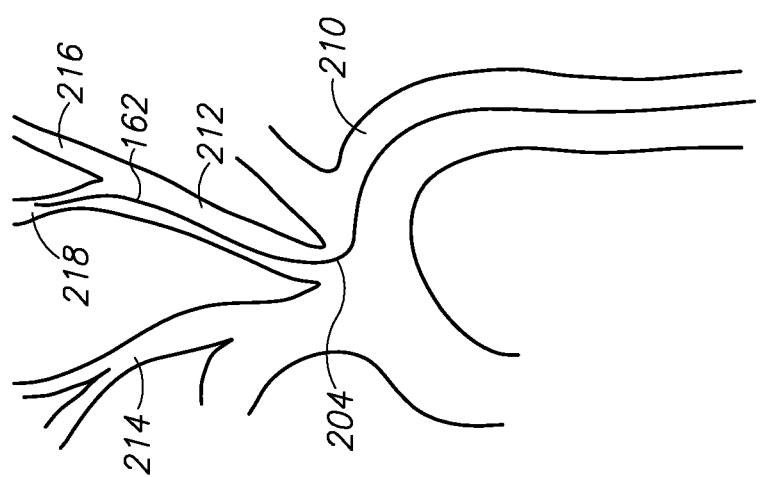

Introduction and positioning of catheter 12 into a selected vessel in the body can be accomplished in various ways. Reference is now made to FIGS. 8A-8H, which are schematic illustrations of a method of positioning catheter 12 in a selected vessel in the body. In the embodiment shown, catheter 12 is positioned in the left internal carotid artery. However, it should be readily apparent that catheter 12 may alternatively be positioned in the right or left common carotid arteries, or any of the internal or external carotid arteries based on the target location. Initially, an incision or puncture is made at a peripheral location, typically the femoral artery, although other locations such as the brachial or radial artery, for example, can be used as well. A guidewire 162 is inserted through the incision and into the vessel, in this case, femoral artery 200, as shown in FIG. 8A. Optionally, as shown in FIG. 8B, a vascular sheath 202 with a dilator portion is introduced over guidewire 162. Vascular sheaths and dilators are commonly known in the art, and are commonly used for providing vascular access to catheters. Once the sheath is in place, the dilator is removed, and a search catheter 204 is introduced over guidewire 162, as shown in FIG. 8C. Search catheter 204 can be, for example, a guiding catheter or an angiography catheter, both of which are types of catheters known in the art, and which include a tip which is pre-shaped in various configurations, suitable for selecting particular vessels. While search catheter 204 is positioned over guidewire 162, the tip of search catheter 204 is relatively straight. Search catheter 204 and guidewire 162 are advanced together through arterial system and into the aortic arch 210, as shown in FIG. 8D. Guidewire 162 is pulled back proximally, which allows for search catheter 204 to assume its bent configuration, suitable for selecting a specific vessel. Search catheter 204 is then used to locate the left common carotid artery 212, as shown in FIG. 8E. Search catheter 204 may alternatively be used to locate the right common carotid artery 214. Guidewire 162 is then advanced into left common carotid artery 212, as shown in FIG. 8F. Search catheter 204 is removed, and guidewire 162 may be advanced further into the left internal carotid artery 218, as shown in FIG. 8G. Alternatively, guidewire 162 may be advanced into an external carotid artery 216, or may remain in the common carotid artery 212, depending on the targeted area. Catheter 12 of the present invention is then introduced over guidewire 162, with the tip of delivery elongated element 22 positioned within the selected vessel, in this case left internal carotid artery 218 as shown in FIG. 8H. Supply elongated element 20 preferably remains within aortic arch 210. This method can be used for a catheter 12 in accordance with any of the described embodiments above.

Figure 9H:
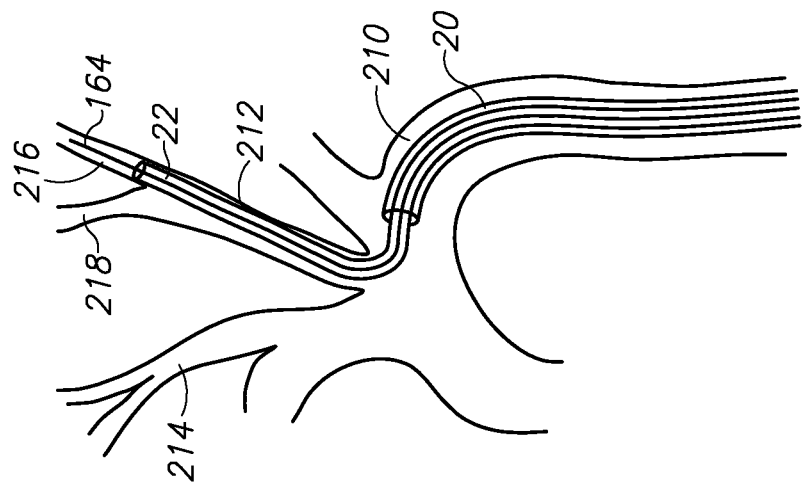
Figure 9G:
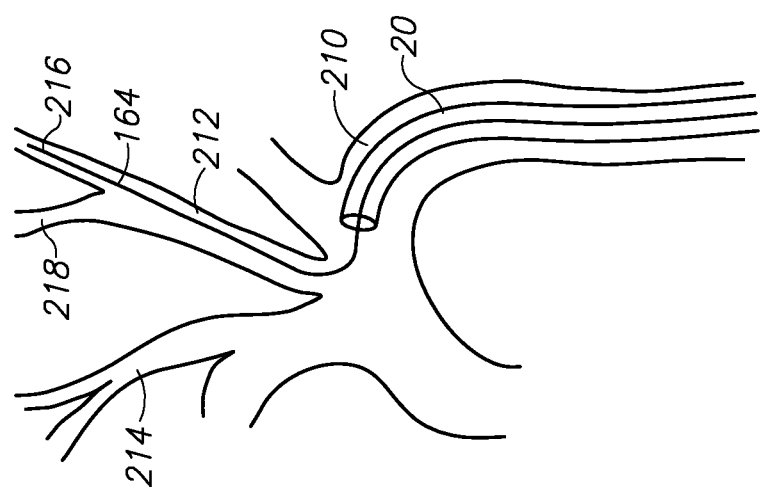

Reference is now made to FIGS. 9A-9H, which are schematic illustrations of the steps of an alternative method of introduction and positioning of catheter 12 into a selected vessel in the body. In this method, an incision or puncture is made as described above, and a long guidewire 164 is introduced into the vessel, in this case, femoral artery 200, as shown in FIG. 9A. Supply elongated element 20, which in at least one embodiment described above (see for example, FIG. 1B) is detachable from the rest of catheter 12, is introduced over guidewire 164, as shown in FIG. 9B. A removable dilator 166 is positioned within supply elongated element 20 to facilitate percutaneous introduction. Supply elongated element 20 is advanced, either with the removable dilator in place or after the removable dilator has been removed, until supply elongated element 20 is in a position within aortic arch 210 proximal to the left common carotid artery 212, as shown in FIG. 9C. If the dilator had not previously been removed, at this point the dilator is removed. Search catheter 204 is then introduced through supply elongated element 20, as shown in FIG. 9D. Guidewire 164 is pulled back proximally, which allows for search catheter 204 to assume its bent configuration, suitable for selecting a specific vessel. Search catheter 204 is then used to locate the left common carotid artery 212, as shown in FIG. 9E. Search catheter 204 may alternatively be used to locate the right common carotid artery 214. Guidewire 164 is then advanced into left common carotid artery 212, as shown in FIG. 9F. Search catheter 204 is removed, and guidewire 164 may be advanced further into the left external carotid artery 216, as shown in FIG. 9G. Alternatively, guidewire 164 may be advanced into an internal carotid artery 218, or may remain in the common carotid artery 212, depending on the desired target. Remaining portions of catheter 12 which are not yet in the vessel are then introduced over guidewire 164, with the tip of delivery elongated element 22 positioned within the selected vessel, in this case left external carotid artery 216. Supply elongated element 20 preferably remains within aortic arch 210. This last step creates assembly of catheter 12 within the desired location.

Figure 10C:
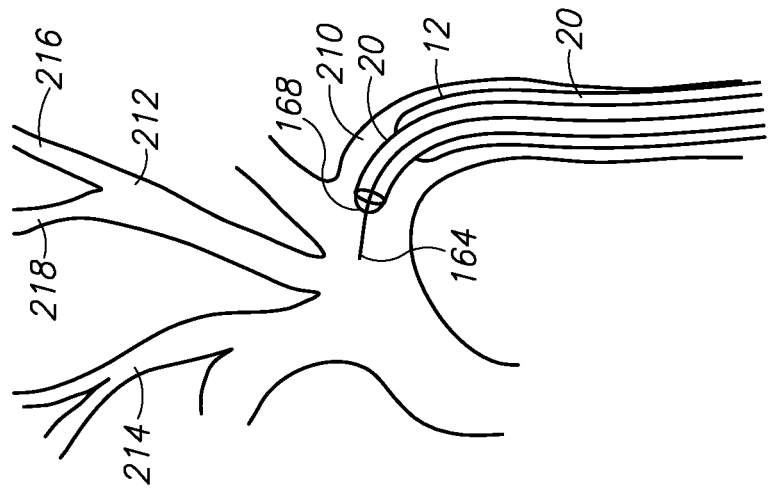
FIGS. 10A-10F are illustrations of the steps of a method of positioning a catheter in a vessel in accordance with yet additional embodiments of the present invention.
Figure 10B:
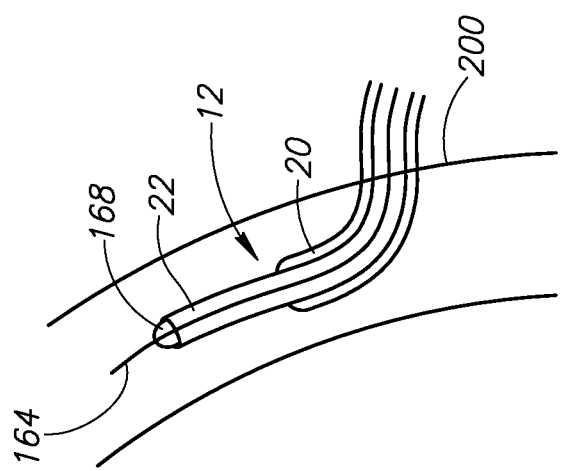
Figure 10A:
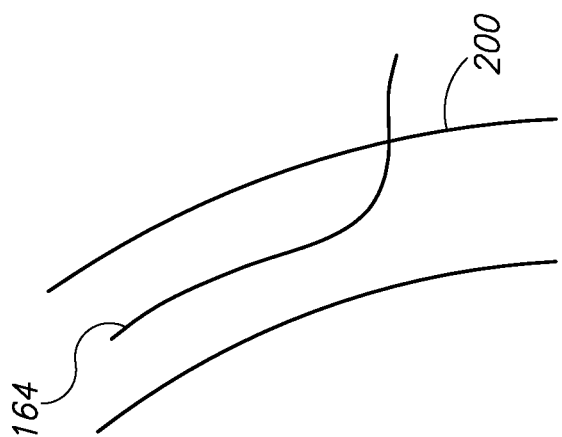
Figure 10F:
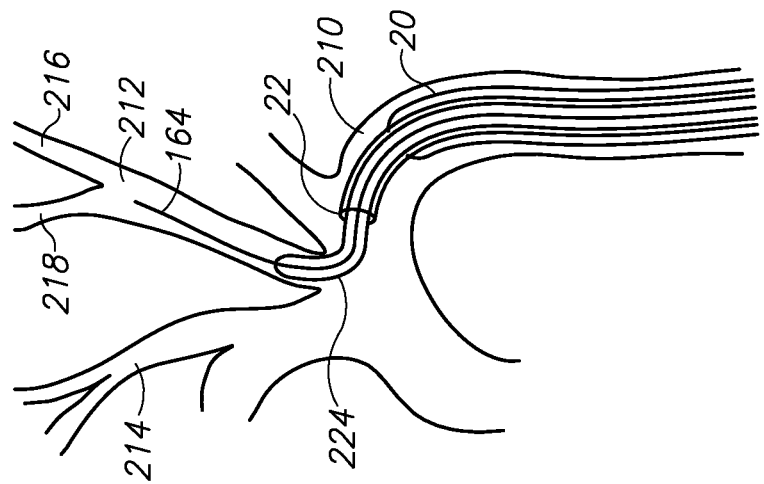
Figure 10E:
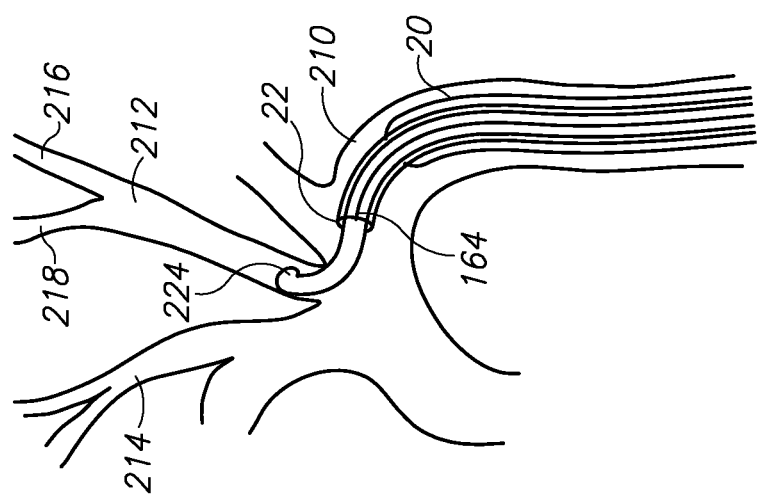
Figure 10D:
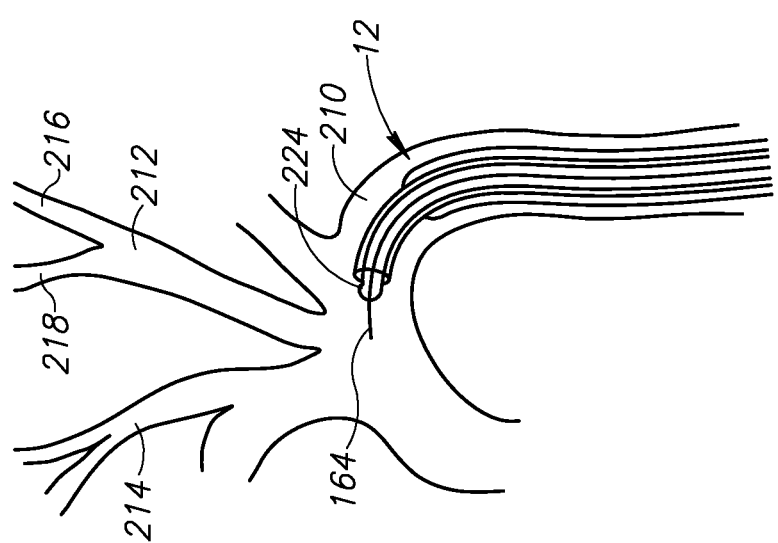

Reference is now made to FIGS. 10A-10F which are schematic illustrations of the steps of an alternative method of introduction and positioning of catheter 12 into a selected vessel in the body. In this embodiment, an incision or puncture is made as described above, and a long guidewire 164 is introduced into the vessel, as shown in FIG. 10A. A dilator 168 is positioned within delivery elongated element 22, and catheter 12 with dilator 168 in place is advanced over guidewire 164, as shown in FIG. 10B. Catheter 12 and dilator 168 are advanced over guidewire 164 into aortic arch 210, as shown in FIG. 10C. When catheter 12 is in position in aortic arch 210, dilator 168 is removed, and a search catheter 224 may then be introduced though delivery elongated element 22, as shown in FIG. 10D. Search catheter 224 is sized to fit within delivery elongated element 22. Alternatively, delivery elongated element 22 may itself be configured with a bent configuration for selecting a vessel, and thus may be used as a search catheter. Guidewire 164 is pulled back proximally, and search catheter 224 or bent delivery elongated element 22 is used to locate the left common carotid artery 212, as shown in FIG. 10E. Search catheter 224 or bent delivery elongated element 22 may alternatively be used to locate the right common carotid artery 214. Guidewire 164 is then advanced into left common carotid artery 212, as shown in FIG. 10F. Search catheter 224 is removed, and guidewire 164 may be advanced further into the left external carotid artery 216. Alternatively, guidewire 164 may be advanced into an internal carotid artery 218, or may remain in the common carotid artery 212, depending on the targeted area of the brain. Catheter 12 is advanced into left common carotid artery 212, with the tip of delivery elongated element 22 positioned within the selected vessel, in this case left external carotid artery 216. Supply elongated element 20 preferably remains within aortic arch 210. For this embodiment, it may be necessary for supply elongated element 20 to have a tapered distal end so as to avoid damage of the vessel during insertion. If inlet ports are positioned along supply elongated element 20, as in FIG. 1A, the distal end 21 of supply elongated element 20 can be tapered by design. If inlet port 26 is located at the distal end 21 of supply elongated element 20, as shown in FIG. 1B, a temporary tapering element can be included at distal end 21. For example, an inflatable balloon may be positioned at distal end 21 of supply elongated element 20, so that during insertion, the balloon can be inflated, providing a tapered edge, and during collection of supply blood, the balloon can be deflated for blood collection.

In all of the described embodiments, positioning of supply elongated element 20 within the vessel should be such that supply blood is collected from retrograde flow of blood. Thus, it is preferable not to advance the supply elongated element 20 into the common carotid artery. Rather, supply elongated element 20 (or at least the inlet ports 26 from supply elongated element 20) should remain in the aorta. If supply elongated element 20 and delivery elongated element 22 are not detachable from one another, supply elongated element 20 may be sized (lengthwise) so as to avoid its entry into the carotid artery. Alternatively, if supply elongated element 20 and delivery elongated element 22 are detachable, a marker on the distal end of supply elongated element 20 may aid in this positioning. In alternative embodiments, catheter 12 may be placed in other locations in the body depending on the desired target area. For example, a renal artery can be targeted to provide cooling/heating to a kidney, or a coronary artery can be targeted to provide cooling/heating to a heart.

Reference is now made to FIGS. 11A-C, which are illustrations of a method for treating a specific target site in accordance with a preferred embodiment of the present invention. As shown in FIG. 11A, catheter 12 is inserted into a blood vessel, and advanced to a vessel which is in fluid communication with the target site, referred to hereinafter as adjacent vessel 100. In a preferred embodiment, wherein the goal is to selectively cool the brain without induction of systemic hypothermia, the target site is the brain, and vessel 100 is the carotid artery (right or left, common, internal or external). A position of catheter 12 within vessel 100 is monitored by visualization of radiopaque marker 48. When catheter 12 is in the desired location, occlusion element 28 is expanded, as shown in FIG. 11B. This expansion primarily serves to isolate a particular section of adjacent vessel 100 which leads to the target site, thereby preventing normothermal blood from flowing into the target organ, and can also help anchor catheter 12 in place. Reference is now made to FIG. 11C, which illustrates the flow of blood. Once occlusion element 28 is deployed, normothermic blood, represented by arrows 44, enters supply elongated element 20 via inlet ports 26. It should be readily apparent that although the method depicted in FIGS. 11A-11C shows supply elongated element 20 having multiple inlet ports and positioned in a vessel in such a way so as to collect antegrade blood, these depictions should not be regarded as limiting. In alternative embodiments, as described above with reference to FIGS. 1B, 8H and 9H, supply elongated element 20 may have one inlet port, and it may be positioned within the aortic arch. Normothermic blood flows through supply lumen 120, out through inlet connector 32 of hub 30 and through supply blood inlet 34 into control unit 14. Control unit 14 then heats or cools the blood to form thermally altered blood, which is pumped out through delivery blood outlet 38, through outlet connector 36, and into delivery elongated element 22. Thermally altered blood, represented by broken arrow 46, flows out through exit port 24 and into the portion of the blood vessel which leads to the target site. In one embodiment, pharmaceuticals are simultaneously administered to the target site via drug infusion port 52. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application. In a preferred embodiment, the cycle is repeated for 1-72 hours.

Reference is now made to FIGS. 12A-C, which are illustrations of a method for treating a specific target site in accordance with another embodiment of the present invention. As shown in FIG. 12A, catheter 12 is inserted into a blood vessel, and advanced to a vessel which is in fluid communication with the target site, referred to hereinafter as adjacent vessel 100. In a preferred embodiment, wherein the goal is to selectively cool the brain without induction of systemic hypothermia, the target site is the brain, and vessel 100 is the carotid artery (right or left, common, internal or external). A position of catheter 12 within vessel 100 is monitored by visualization of radiopaque marker 48. When catheter 12 is in the desired location, occlusion element 28 and second occlusion element 54 are both expanded, as shown in FIG. 12B. Occlusion element 28 and second occlusion element 54 can be sequentially or simultaneously expanded. Expansion of occlusion element 28 primarily serves to isolate a particular section of blood vessel 100 which leads to the target site, and can also help anchor catheter 12 in place. Expansion of second occlusion element 54 serves to separate an area for delivery of supplemental blood, which is of a different temperature $T_2$ than a temperature $T_1$ of thermally treated blood sent to the target site, and from normothermic blood returning through supply elongated element 20. Reference is now made to FIG. 12C, which illustrates the flow of blood. Once occlusion element 28 and second occlusion element 54 are deployed, normothermic blood, represented by arrows 44, enters supply elongated element 20 via inlet ports 26. It should be readily apparent that although the method depicted in FIGS. 12A-12C shows supply elongated element 20 having multiple inlet ports and positioned in a vessel in such a way so as to collect antegrade blood, these depictions should not be regarded as limiting. In alternative embodiments, as described above with reference to FIGS. 1B, 8H and 9H, supply elongated element 20 may have one inlet port, and it may be positioned within the aortic arch. Normothermic blood flows through supply lumen 120, out through inlet connector 32 of hub 30 and through supply blood inlet 34 into control unit 14. Control unit 14 then heats or cools the blood to form thermally altered blood, which is pumped out through delivery blood outlet 38, through outlet connector 36 and into delivery elongated element 22. Thermally altered blood, represented by broken arrow 46, flows out through exit port 24 and into the portion of the blood vessel which leads to the target site. In addition, supplemental blood, represented by wide arrows 47, is sent through auxiliary delivery elongated element 23 and into a secondary vessel 101, which may lead to a secondary target site. In one embodiment, pharmaceuticals are simultaneously administered to the target site and/or to the supplemental blood via drug infusion port 52. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application.

Figure 13C:
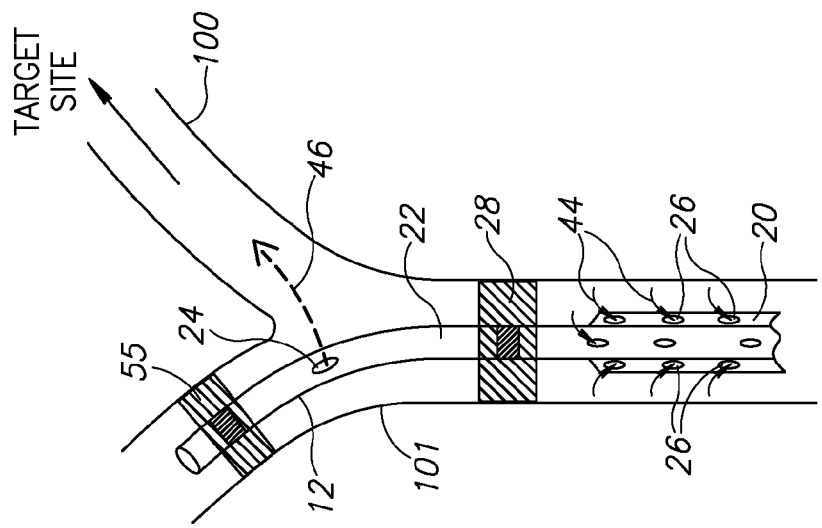
FIGS. 13A-13C are illustrations of a method for treating a specific target site in accordance with yet another embodiment of the present invention.
Figure 13B:
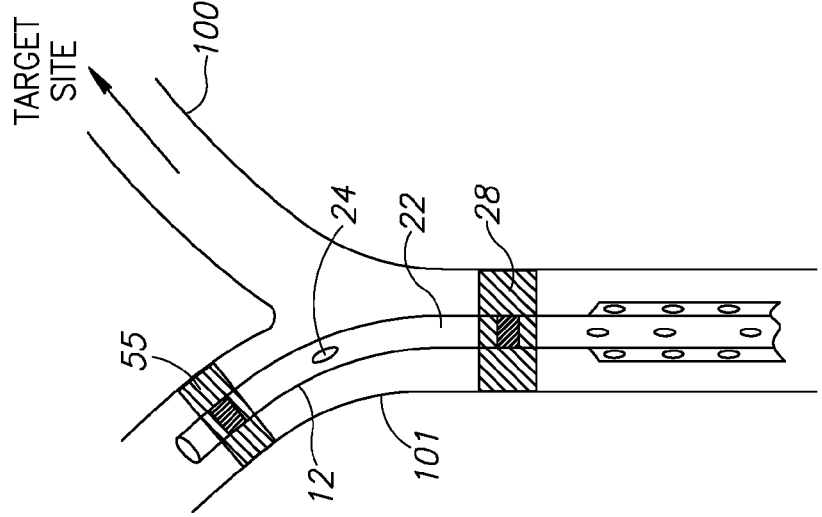
Figure 13A:
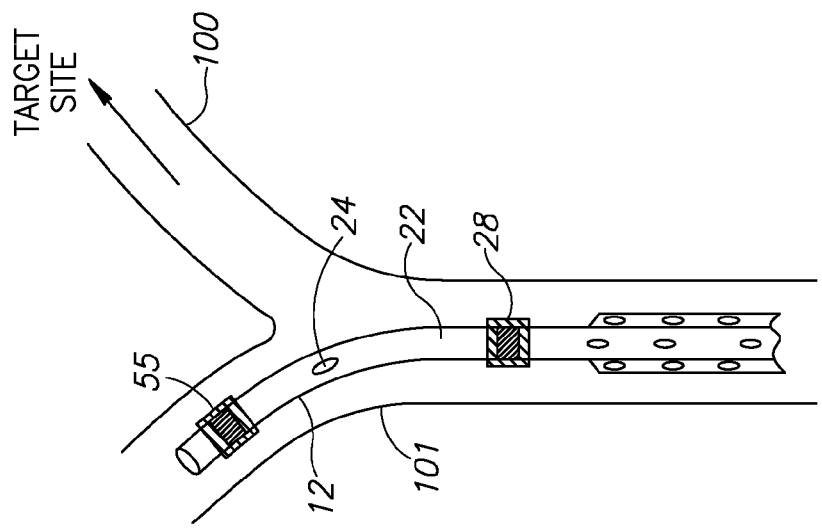

Reference is now made to FIGS. 13A-C, which are illustrations of a method for treating a specific target site in accordance with yet another embodiment of the present invention. As shown in FIG. 13A, catheter 12 is inserted into a blood vessel, and advanced to a secondary vessel 101 which is near vessel 100. For example, vessel 100 and secondary vessel 101 can be branches of a main vessel. This method may be desirable, for example, if vessel 100 is diseased and might be adversely affected by introduction of a foreign element such as a catheter therein. In a preferred embodiment, wherein the goal is to selectively cool the brain without induction of systemic hypothermia, the target site is the brain, and secondary vessel 101 is the carotid artery (right or left, common, internal or external). A position of catheter 12 within vessel 101 is monitored by radiopaque marker 48. When catheter 12 is in the desired location, occlusion element 28 and distal occlusion element 55 are expanded, as shown in FIG. 13B. Expansion of occlusion elements 28 and 55 serves to isolate blood vessel 100 which leads to the target site, and anchors catheter 12 in place without placing catheter 12 directly in blood vessel 100. Reference is now made to FIG. 13C, which illustrates the flow of blood. Once occlusion elements 28 and 55 are deployed, normothermic blood, represented by arrows 44, enters supply elongated element 20 via inlet ports 26. It should be readily apparent that although the method depicted in FIGS. 12A-12C shows supply elongated element 20 having multiple inlet ports and positioned in a vessel in such a way so as to collect antegrade blood, these depictions should not be regarded as limiting. In alternative embodiments, as described above with reference to FIGS. 1B, 8H and 9H, supply elongated element 20 may have one inlet port, and it may be positioned within the aortic arch. Normothermic blood flows through supply lumen 120, out through inlet connector 32 of hub 30 and through supply blood inlet 34 into control unit 14. Control unit 14 then heats or cools the blood to form thermally altered blood, which is pumped out through delivery blood outlet 38, through outlet connector 36, and into delivery elongated element 22. Thermally altered blood, represented by broken arrow 46, flows out through exit port 24 and into the portion of the blood vessel which leads to the target site. In one embodiment, pharmaceuticals are simultaneously administered to the target site via drug infusion port. In another embodiment, sensors located at or near the exit ports measure physiological parameters such as pressure, flow and temperature, and the data is sent to control unit 14. Control unit 14 compares the received data to desired settings and adjusts heating/cooling as required. This cycle can continue for as long as is necessary for the particular application.

It should be readily apparent that a single catheter serves to both collect and deliver the normothermic and thermally altered blood. In an additional embodiment, all or some blood contact surfaces can be coated with an anti thrombotic substance such as heparin.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A catheter system comprising:
    an outer elongated element having an outer elongated element proximal end and an outer elongated element distal end, said outer elongated element having an outer elongated element lumen extending from said outer elongated element proximal end to said outer elongated element distal end and having an outlet port at said outer elongated element distal end, and a proximal occlusion element located at said outer elongated element distal end, said proximal occlusion element proximal to said outlet port;
    an inner elongated element having an inner elongated element proximal end and an inner elongated element distal end, and a distal occlusion element located at said inner elongated element distal end, said inner elongated element positioned within said outer elongated element lumen wherein said outer elongated element is coaxially arranged with respect to said inner elongated element, said coaxial arrangement providing a delivery lumen between said inner and outer elongated elements for delivery of a substance to a vessel through said delivery lumen and through said outlet port, wherein said inner elongated element distal end is distal to and movable with respect to said outer elongated element distal end, and wherein said inner elongated element further comprises a blood-release element at said inner elongated element distal end; and
    a guidewire positioned through said blood-release element, wherein when said guidewire is positioned through said blood-release element, said blood-release element remains at least partially open to blood-flow.

2. The catheter system of claim 1 wherein said inner elongated element further comprises a core wire extending from and attached to said inner elongated element distal end and extending to and attached to said inner elongated element proximal end.

3. The catheter system of claim 2, wherein said core wire is sandwiched between polymeric layers of a shaft of said inner elongated element.

4. The catheter system of claim 1, wherein said inner elongated element is removable from said outer elongated element during a procedure.

5. The catheter system of claim 1, wherein said inner elongated element comprises an inner elongated element lumen extending from said inner elongated element proximal end to said inner elongated element distal end.

6. The catheter system of claim 5 wherein said guidewire is further positioned within said inner elongated element lumen.

7. The catheter system of claim 1, wherein said substance is a therapeutic or diagnostic agent introduced into said outer elongated element lumen, and positioned between an outer wall of said inner elongated element and an inner wall of said outer elongated element, and positioned between said distal and proximal occlusion elements when introduced into a vessel.

8. The catheter system of claim 1, further comprising a hub at said outer elongated element proximal end, said hub configured for introducing a delivery substance into said outer elongated element lumen.

9. The catheter system of claim 8, wherein said hub is further configured for introducing inflation fluid to said proximal occlusion element.

10. The catheter system of claim 8, wherein said hub is further configured for introducing said inner elongated element through said outer elongated element lumen.

11. The catheter system of claim 1, wherein said blood-release element has an inner diameter which is approximately 0.002" greater than a diameter of said guidewire.

12. The catheter system of claim 1, wherein said blood-release element comprises a separate distal element positioned distal to said distal occlusion element.

13. The catheter system of claim 1, wherein said blood-release element comprises an opening at a proximal end of said distal occlusion element, said opening providing an outlet for blood-flow in a substantially axial direction.

14. The catheter system of claim 1, wherein said blood-release element comprises a separate element having a proximal end, a distal end, and a lumen therein, said lumen extending from proximal end to distal end of said distal occlusion element.

15. The catheter system of claim 1, wherein said distal occlusion element is a fixed wire balloon.

16. The catheter system of claim 1, further comprising a guidewire positioned through said outer elongated element.

17. The catheter system of claim 1, wherein said inner elongated element comprises an exposed portion having an exposed portion proximal edge at a proximal occlusion element distal end and an exposed portion distal edge at a distal occlusion element proximal end, and wherein said exposed portion has a length extending from said exposed portion proximal edge to said exposed portion distal edge, wherein said length may be varied by moving said inner elongated element with respect to outer elongated element.

18. The catheter system of claim 1, wherein said outlet port comprises multiple outlet ports.

19. The catheter system of claim 1, wherein said outlet port is created by the coaxial arrangement of said outer and inner elongated elements.

* * * * *